(12) United States Patent
Lauer

(10) Patent No.: US 8,991,876 B2
(45) Date of Patent: Mar. 31, 2015

(54) CONNECTION MEANS AND METHOD FOR CONNECTING AT LEAST TWO FLUID-CONDUCTING MEDICAL-TECHNICAL SYSTEMS, AS WELL AS MEDICAL-TECHNICAL APPARATUS

(75) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 748 days.

(21) Appl. No.: 12/765,933

(22) Filed: Apr. 23, 2010

(65) Prior Publication Data

US 2010/0270792 A1 Oct. 28, 2010

Related U.S. Application Data

(60) Provisional application No. 61/185,687, filed on Jun. 10, 2009.

(30) Foreign Application Priority Data

Apr. 23, 2009 (DE) .......................... 10 2009 018 664
Jun. 10, 2009 (DE) .......................... 10 2009 024 575

(51) Int. Cl.
*F16L 7/00* (2006.01)
*A61M 39/10* (2006.01)
*A61M 39/18* (2006.01)
*A61M 1/14* (2006.01)

(52) U.S. Cl.
CPC ............... *A61M 39/10* (2013.01); *A61M 39/18* (2013.01); *A61M 1/14* (2013.01); *A61M 2039/1072* (2013.01); *Y10S 604/905* (2013.01)
USPC ...... 285/374; 285/261; 285/123.12; 604/535; 604/905

(58) Field of Classification Search
USPC ......... 285/374, 371, 261, 146.3, 224, 123.12; 604/905, 535, 536, 537, 6.1, 6.11
See application file for complete search history.

(56) References Cited

U.S. PATENT DOCUMENTS

| 72,258 | A | * | 12/1867 | Abbot | 285/147.1 |
| 1,017,813 | A | * | 2/1912 | Schuermann | 285/261 |
| 1,490,622 | A | * | 4/1924 | Miller | 285/146.1 |
| 3,796,057 | A | * | 3/1974 | Dougherty | 285/371 |
| 3,986,508 | A | * | 10/1976 | Barrington | 604/905 |
| 4,019,512 | A | * | 4/1977 | Tenczar | 604/905 |
| 4,153,278 | A | * | 5/1979 | Ahlstone | 285/146.3 |
| 5,308,314 | A | * | 5/1994 | Fukui et al. | 604/6.11 |
| 5,492,147 | A | * | 2/1996 | Challender et al. | 604/905 |

(Continued)

FOREIGN PATENT DOCUMENTS

DE 19828651 A1 12/1999
DE 10 2009 012 632.5 A1 9/2010

(Continued)

OTHER PUBLICATIONS

PCT International Search Report for PCT/EP2010/002323, mailed on May 31, 2011.

*Primary Examiner* — David E Bochna
(74) *Attorney, Agent, or Firm* — Kenyon & Kenyon LLP

(57) ABSTRACT

A connection for the fluid connection of at least one first fluid-conducting, medical-technical system to a second one, a method for connecting at least two fluid-conducting, medical-technical systems, as well as an external medical-technical apparatus and a medical-technical apparatus are described.

33 Claims, 26 Drawing Sheets

(56) References Cited

U.S. PATENT DOCUMENTS

| | | | | |
|---|---|---|---|---|
| 5,643,190 A * | 7/1997 | Utterberg | ..................... | 604/905 |
| 5,807,347 A | 9/1998 | Bonaldo | | |
| 5,911,710 A * | 6/1999 | Barry et al. | ................... | 604/249 |
| 6,009,339 A * | 12/1999 | Bentsen et al. | ................ | 600/322 |
| 6,050,978 A * | 4/2000 | Orr et al. | ...................... | 604/905 |
| 6,059,325 A * | 5/2000 | Heckele et al. | ................ | 285/325 |
| 6,063,062 A * | 5/2000 | Paradis | .......................... | 604/256 |
| 6,745,998 B2 * | 6/2004 | Doyle | ............................ | 604/241 |
| 6,814,726 B1 * | 11/2004 | Lauer | ............................ | 604/905 |
| 7,396,051 B2 * | 7/2008 | Baldwin et al. | ............... | 604/905 |
| 7,465,285 B2 * | 12/2008 | Hutchinson et al. | ......... | 604/6.01 |
| 7,476,209 B2 * | 1/2009 | Gara et al. | ..................... | 604/6.1 |
| 7,763,013 B2 * | 7/2010 | Baldwin et al. | ............... | 604/905 |
| 7,766,304 B2 * | 8/2010 | Phillips | ......................... | 604/905 |
| 7,784,835 B1 * | 8/2010 | Keays et al. | ................... | 285/261 |
| 7,811,278 B2 * | 10/2010 | Knipple et al. | ............... | 604/535 |
| 8,100,866 B2 * | 1/2012 | Peppel | ........................... | 604/6.1 |
| 8,192,421 B2 * | 6/2012 | Lopez et al. | ................... | 604/533 |
| 8,197,452 B2 * | 6/2012 | Harding et al. | ............... | 604/246 |
| 8,220,843 B2 * | 7/2012 | More et al. | ................. | 285/146.3 |
| 2004/0199143 A1 | 10/2004 | Lauer | | |
| 2005/0230292 A1 | 10/2005 | Beden et al. | | |
| 2006/0189961 A1 | 8/2006 | Miyahara | | |
| 2008/0103487 A1 | 5/2008 | Miyasaka | | |
| 2010/0133153 A1 | 6/2010 | Beden et al. | | |

FOREIGN PATENT DOCUMENTS

| | | |
|---|---|---|
| DE | 10 2009 012 633.3 A1 | 9/2010 |
| DE | 10 2009 018 664.6 A1 | 10/2010 |
| DE | 10 2009 024 468.9 A1 | 12/2010 |
| EP | 0966985 | 6/1999 |
| EP | 1 566 196 A1 | 8/2005 |
| EP | 1 649 890 A1 | 4/2006 |
| JP | 55-23213 A | 2/1980 |
| JP | 2000-033124 A | 2/2000 |
| JP | 2004-141646 A | 5/2004 |
| JP | 2012-506381 A | 3/2012 |
| WO | 03/101510 A1 | 12/2003 |
| WO | 2006-037638 A1 | 4/2006 |
| WO | 2010/102784 A1 | 9/2010 |
| WO | 2010/102790 A1 | 9/2010 |

* cited by examiner

US 8,991,876 B2

CONNECTION MEANS AND METHOD FOR CONNECTING AT LEAST TWO FLUID-CONDUCTING MEDICAL-TECHNICAL SYSTEMS, AS WELL AS MEDICAL-TECHNICAL APPARATUS

CROSS REFERENCE TO RELATED APPLICATIONS

This application claims the benefit of U.S. Provisional Application No. 61/185,687 filed Jun. 10, 2009, and claims priority to German Patent Application No. 10 2009 024 575.8 filed Jun. 10, 2009 and German Patent Application No. 10 2009018 664.6 filed Apr. 23, 2009, all of which are herein incorporated by reference in their entirety.

FIELD OF INVENTION

The present invention relates to a connection means. It further relates to a method for connecting at least two fluid-conducting medical-technical systems, as well as an external medical-technical functional means and a medical-technical apparatus. Furthermore it relates to a drip-protection means and a closure sleeve.

BACKGROUND OF THE INVENTION

External functional means are regularly employed with treatment and analytic apparatuses in medical or laboratory technology. Such external functional means, which may be based on tube systems and cassette arrangements, are frequently connected to the treatment and analytic apparatus and/or to another external functional means by establishing a fluid connection for liquids and/or gases.

SUMMARY OF THE INVENTION

It is an object of the present invention to provide a further connection means for the fluid connection between at least two fluid-conducting medical systems (in the following also in short: system or systems).

In the entirety of the following discussion, the use of the expression "may be or have" should be understood to be synonymous with "preferably is or has."

The connection means of the invention serves for the fluid connection of at least one first fluid-conducting system and a second fluid-conducting system (further below also referred to as a connection system) and comprises at least one first pipe section of the first system which is intended to be connected to a second pipe section of the second system.

By means of the connection of the two pipe sections a fluid connection between two systems may advantageously be established. The respective systems may each be an external functional means and/or a treatment apparatus between which a fluid connection is to be established.

The expression "pipe" or "pipe section" as presently used designates a pipe passage or a pipe conduit suited and intended for receiving and/or passing on fluids.

Thus, in a preferred embodiment in accordance with the invention, the first or the second pipe or pipe section comprises at least one inner pipe and at least one outer pipe. The inner pipe is arranged in an interior of the outer pipe. The inner pipe and the outer pipe may have a concentric or non-concentric arrangement relative to each other.

The inner pipe and the outer pipe may be arranged on an external functional means or on a treatment apparatus, or may be provided for being arranged there.

The connection means may be suited for receiving at least one portion of the connection pipe of a treatment apparatus or of an external functional means between the inner pipe and the outer pipe.

The expression "connection pipe" designates a pipe, a pipe section, a passage, a conduit or the like, which is adapted to be connected or is connected to the connection means of the invention.

In each embodiment in accordance with the invention, the connection pipe may be flexible or rigid.

The connection pipe may be received by a portion thereof in an interstice between the inner pipe and the outer pipe of the connection means.

A fluid connection may be provided between an interior of the inner pipe and an interior of the outer pipe.

The first and/or the second system may be a respective external medical-technical functional means, medical-technical treatment or blood treatment apparatus, medical analytic apparatus, or the like systems conducting medical fluids (in particular liquids and gases).

The connection means may comprise a closure means for short-circuiting the inner lumen and the annular gap between the inner pipe and the outer pipe for the purpose of rinsing and/or disinfecting all of the inner surfaces of the system getting into contact with fluid.

The connection means may comprise a widening for connecting—in particular by jamming or expanding—the inner pipe against the connection pipe. The widening may be present on the inner pipe or on the connection pipe. It may be present as a result of integral manufacture with the inner pipe or the connection pipe, or may have been connected to the latter. It may have a spherical or convex outer surface. It may be intended to effect a fluidic seal between inner pipe and connection pipe in the ready-to-use, connected condition of the connection means.

The widening may have a spherical and/or globular and/or curved and/or arc-shaped and/or convex outer surface, in particular in a region of the maximum cross-section or diameter, preferably in a direction of flow.

The widening may be configured so as to effect a fluidic seal between the first pipe section and the second pipe section, in particular between inner pipe and connection pipe, in the ready-to-use, connected condition of the connection means.

The widening may have its largest cross-sectional diameter or its largest circumference in a cross-section in a plane perpendicular to the direction of connection of the first pipe section to the second pipe section, in a region of the widening that is central in the direction of connection. The direction of connection may be an axial direction of the pipe section to which the widening is connected.

The widening may have its largest cross-sectional diameter or its largest circumference in a cross-section in a plane perpendicular to a direction of extension of the inner lumen of the one pipe section to which the widening is connected, in a region of the widening that is central in the direction of connection.

The widening may have the same diameter and/or circumference in at least three different sectional planes through a central point of the widening or in at least three different sectional planes containing a common straight line.

The diameter or the cross-sectional diameter of the widening may be circular.

The widening may be configured such that it may be moved, in the process of connecting the first pipe section to the second pipe section, along a displacement path in the pipe section into which it is being introduced, while maintaining the sealing condition brought about by it, and/or may be configured such that it may be tilted, in the process of connecting the first pipe section to the second pipe section or following completion of connecting, by an angle relative to the direction of flow, while maintaining the sealing condition brought about by it. In their connected condition, the connected pipe sections may therefore be telescoped some further distance in an inward or outward direction without having to relinquish the connected condition obtained by means of the widening. Likewise, the connected pipe sections may be tilted slightly relative to each other or be folded jointly in their connection to each other without relinquishing the connected condition or causing a leakage.

The widening may be configured such that it may be moved, in the process of connecting the first pipe section to the second pipe section, along a displacement path in the pipe section into which it is being introduced, while maintaining the sealing condition brought about by it. The displacement path may be 1, 2, 3, 4, 5, 6, 7, 8, 9, 10 or more millimeters (mm).

The widening may be configured such that it may be tilted, in the process of connecting the first pipe section to the second pipe section or following completion of connecting, by an angle relative to the direction of flow while maintaining the sealing condition brought about by it. The angle may be in a range from 1 to 3 degrees; it may be in a range from 1 to 5 degrees, 1 to 8 degrees, or 1 to 10 degrees. It may adopt numeric values of 1, 2, 3, 4, 5, 6, 7, 8, 9, or 10 degrees or more.

The connection means of the invention may comprise another, second sealing means. In a condition of use of the connection means, this second sealing means may be arranged adjacent to the widening.

The connection means may comprise a pressure limiting valve. It may comprise a waste water branch.

The connection means may comprise a pivotal mount for lateral and/or horizontal alignment of the inner pipe and/or of the outer pipe and/or of the connection pipe relative to each other.

In addition to other centering or aligning means, the connection means may comprise a pre-centering means for—vertical and/or lateral—alignment of the inner pipe and/or of the outer pipe and/or of the connection pipe prior to establishing the fluid connection.

The pre-centering means may comprise at least two springily deflectable tongues.

The connection means may comprise a touch-prevention panel for preventing an interior from being contaminated and/or the connection pipe from being touched by a user.

The touch-prevention panel may be retained in the external, medical-technical functional means by a latching arrangement. It may comprise a plurality of bendable segments. A number of bendable segments may be bendable independently of other segments.

The connection means may comprise a means which is mechanically altered and/or moved in the process of connecting such that the effected connection continues to be apparent on the means following disconnection. This means may be the touch-prevention panel.

The connection means may comprise a bellows arrangement. This may be part of the outer pipe. The outer pipe may comprise at least one spring member for tightening the bellows arrangement.

The connection means may comprise a means for moving the closure means, for example a removable rinsing cap, for exposing an opening of the inner pipe in order to establish the fluid connection. The rinsing cap may be adapted to be moved automatically for exposing with the aid of the means.

The inner pipe and the outer pipe may be arranged for axial displacement relative to each other. The connection means may comprise a means—in particular an automatic means—for axially displacing the inner pipe and/or the outer pipe relative to each other.

The connection means may comprise a means for axially displacing both the inner pipe and the outer pipe. In the displacement achievable hereby, the relative position of inner pipe and outer pipe may remain unchanged or may change.

Materials participating in the realization of the range of flow of the fluid connection to be obtained may be hydrophilic. As an alternative, or in addition, surfaces in the range of flow may have a hydrophilic coating.

The connection means of the invention may be employed, for example, as an automatic substitute connector.

Coupling may take place through the intermediary of a sliding guide or by making use of the fact that the rinsing cap will be pivoted whenever the connection means is in the pivoting position.

An execution with other types of drive mechanisms (mechanical, e.g., rack/pinion, or pneumatic) is encompassed by the invention.

The connection means of the invention and/or the medical-technical apparatus of the invention may comprise sensors for detecting positions or attitudes of single elements of the connection means (for example of inner pipe, outer pipe, rinsing cap, connection pipe, etc.).

The sensor apparatuses used may equally be based on various principles (axial detection of position, e.g., with the aid of photoelectric barriers or detection of the spindle's rotation, detection of the pivoting movement also with the aid of photoelectric barriers, switches, rotary potentiometers, and the like).

The liquid flowing through the connection means of the invention in the connected condition of a disposable may first of all be utilized for filling and rinsing the external functional means, and later on during the treatment as a substitute.

A fully automatic connection, e.g., of a dialyzer (or of a rinse port) is equally encompassed by the invention.

The object of the invention is equally achieved through an external, medical-technical functional means in accordance with the invention. All of the advantages that may be obtained through the connection means of the invention may also be obtained in an undiminished manner with the external functional means of the invention.

An "external functional means" may be a single-use component or a single-use article. It may be made of a plastic material.

The external functional means of the invention may be intended for use in a treatment method. Treatment methods within the meaning of the present invention include medical or medical-technical treatment methods as well as analytic methods in laboratory technology.

In a preferred embodiment, the external functional means of the invention is configured as a blood cassette.

A blood cassette within the meaning of the present invention is, for example, described in the German Patent Application No. 10 2009 018 664.6 (representative's file FM19A27) and German Patent Application No. 10 2009 024 468.9. (09/33-d01 DE; FM19B27) filed by the applicant of the present invention with the German Patent and Trademark Office on Apr. 23, 2009 and Jun. 10, 2009, respectively, and each having the title "Externe Funktionseinrichtung, Blutbehandlungsvorrichtung zum Aufnehmen einer erfindungsgemäßen externen Funktionseinrichtung, sowie Verfahren" [External functional means, blood treatment apparatus for receiving an external functional means in accordance with the invention, and method], the respective disclosures of which are herewith fully incorporated by way of reference.

The object of the invention is equally achieved through a method in accordance with the invention. All the advantages of the connection means of the invention may also be obtained in an undiminished manner with the method of the invention.

In the method of the invention for connecting at least two fluid-conducting medical-technical systems, at least one connection means of the invention is used.

In the method, an expansion of the inner lumen of the connection pipe by means of the widening of the inner pipe may take place, to thereby obtain a fluid-tight connection.

The method may further include performing an automatic routine for determining possibly existing leakages of the fluid connection obtained with the aid of the connection means and/or the operation of a pressure limiting valve of the connection means.

In the method of the invention, the rinsing cap may be pivoted automatically for exposing the inner pipe in order to establish the fluid connection.

The object of the invention is also achieved through a treatment apparatus of the invention. All the advantages of the connection means of the invention may in turn be achieved in an undiminished manner with the treatment apparatus of the invention.

In a preferred embodiment of the present invention, the treatment apparatus is a blood treatment apparatus such as a dialyzing apparatus, for performing a dialysis treatment such as a hemodialysis, hemofiltration, hemodiafiltration, and the like.

The treatment apparatus may equally be suited for performing a peritoneal dialysis.

The object of the invention is also achieved through a drip-protection means and a closure sleeve.

The connection means of the invention may advantageously serve for automatically establishing a connection between two fluid-conducting systems, in particular for a liquid. This may provide the advantage that during the connection, the user will in principle not get into contact with parts that get into contact with fluid or liquid. In this way, a contamination of the location of connection and/or of the conveyed fluid may advantageously be reduced or precluded during the connection.

Apart from this, the user may advantageously be relieved; the user needs not to undergo training. Furthermore the risk of an error or even damage-causing connection is eliminated.

The connecting operation may be integrated into an automated overall operation that may be carried out without intervention by the user (e.g.: initial testing of the machine with subsequent filling/rinsing).

As a result of arranging the inner pipe of the connection means concentrically, sterility or hygiene of the connecting location may advantageously be preserved.

As a result of the method of the invention it may advantageously be possible to keep the treatment apparatus and the external functional means at the same time free from germs and/or foreign matter. A mutual contamination may be avoided.

By means of the connection means of the invention it is advantageously possible to ensure a substantially complete access involving low pressure losses to any surfaces of the external functional means to be sterilized, which is generally required for sterilization methods utilizing gas.

Closing the connection means in an automatic and/or automated manner may moreover advantageously avoid trickling out of residual liquid quantities from the connection openings after termination of a treatment procedure.

By employing the touch-prevention panel described herein, the connection means of the invention and/or the external functional means of the invention may advantageously be equipped with a reuse prevention means. In particular, it represents a tamper protection advantageously indicating in an easily recognizable form that the external functional means was already used.

The connection means of the invention may advantageously enable to ensure maximum possible filling and/or draining processes through rheologically appropriate configuration and arrangement of any fluid-conducting regions (also in short: fluid regions), in particular of the inner pipe, of the outer pipe and of the connection pipe. In this way, it may advantageously also be ensured that a minimum possible residual quantity of liquid remains in the fluid system of the treatment apparatus used, with no liquid at all or only very little liquid leaking out into the environment of the connection opening.

As the inner lumen of the inner pipe may be partly emptied or may have no liquid content at all at the time of removing the rinsing cap, it is thus advantageously possible to reduce or even avoid the risk of projected droplets of liquid—which might at the last moment, during removal of the rinsing cap, still have contact with non-sterile zones of the outer pipe and/or of the rinsing cap—mixing with sterile residual liquids in the connection means and thus possibly being transferred into the inner lumen of the inner pipe upon repeated connection to the connection partner.

Furthermore, the connection means of the invention may also advantageously ensure freedom from dead spaces and/or stationary eddies. This may be of particular advantage during sterilization.

In the case of a horizontal connection assembly the inner lumen and the outer lumen generally remain filled with rinsing solution following rinsing. This implies the risk of at least small quantities of liquid getting into the environment every time the closure cap or rinsing cap is removed manually. This may advantageously be avoided with the connection means of the invention.

In accordance with the invention, using the closure cap or rinsing cap of the connection means of the invention may advantageously result in the avoidance of secondary spaces. This allows simplified and particularly thorough disinfection and rinsing.

In addition, in accordance with the invention the rinsing cap is preferably adapted in a rheologically favorable manner on the inside, so that all of the flow regions may advantageously be rinsed to a sufficient extent or degree during disinfection and rinsing.

A corresponding—e.g. conical—configuration of the inner pipe furthermore advantageously allows to ensure that critical sealing regions are subjected to particularly intense disinfection and rinsing. As a result of the rotational flow achievable due to the configuration, it is possible to reach even narrow joints while at the same time creating the rheological preconditions for a return flow of the fluids via the outer lumen.

The connection means of the invention may advantageously provide a realization of all relevant areas that provides maximum possible safety against touch and—where possible—even coughing.

The connection means of the invention may furthermore advantageously be configured to be particularly intolerant of tolerances. This is advantageously true both for tolerances within the single partial arrangements of treatment apparatus and external functional means and for the tolerance compatibility of the two connection partners or fluid systems among each other. Both in manual and automated execution of the actual connecting operation, it is thus advantageously possible to provide a maximum possible—in particular lateral—tolerance of the connection partners before and during the connection and to also admit a maximum possible tolerance for the sliding movements in the direction of connecting. As a combination of both tolerances, a sufficient angular tolerance among the axes of connection of the two connection partners may advantageously be provided.

During the connection, the connection means of the invention advantageously provides sufficient tightness until termination of the treatment. With the aid of the second redundant seal, i.e. the redundancy sealing bead, the connection means of the invention is advantageously capable of counteracting the case of a leakage occurring nevertheless. In addition, in accordance with the invention it is advantageously possible to detect leaked liquid and discharge it in a controlled manner.

In order to counteract the stress of a transversal mechanical force among the connection partners during the connection, the connection means of the invention advantageously provides a design of the arrangement involving low transversal forces, in particular with concurrent action of gravity and by making use of the maximum lateral tolerance.

By means of the connection means of the invention, the treatment apparatus is advantageously protected against undesired access to the connection regions, so that maintenance and/or inspection of these regions may advantageously be reduced. In this way, it may advantageously be possible to reduce the costs required for maintenance of the treatment apparatus.

Moreover, all of the components of the treatment apparatus that are relevant for the connection arrangement may advantageously be inspected and/or exchanged easily.

In order to obtain a fluid communication in accordance with the invention it is moreover advantageously possible to do without the use of costly materials such as, e.g., silicone rubber. In this way, the manufacturing costs may advantageously be reduced.

With the connection means of the invention, it is furthermore possible to avoid elastomer seals in the range or area of the treatment apparatus. In this way, it is advantageously possible to avoid boundary zones and/or dead space zones between the elastomer seals and their installation spaces that are otherwise poorly suited for rinsing through. By replacing the elastomer seals that were previously subjected to abrasion during connections with low-wear, non-elastomer sealing arrangements, it is furthermore advantageously possible to clearly extend maintenance cycles.

In addition, when the connection means of the invention is provided on the side of an external functional means, the outer pipe is advantageously protected against touch following removal of the rinsing cap or protective cap, and so is the outer pipe of the connection means on the side of the treatment apparatus. In this way it is equally advantageously possible to avoid transfer or introduction of germs into the inner pipe during the connection to the treatment apparatus.

A first embodiment represents an automatically connecting arrangement between an external functional means and a treatment apparatus.

Here, the connection means of the invention is customarily configured and provided as a part of the treatment apparatus.

Such an arrangement may be usable in a particularly advantageous manner in connections between external functional means and treatment apparatuses where several three-dimensionally defined connections between external functional means and treatment apparatus should or have to be achieved simultaneously.

Such an arrangement may, for example, be provided for an automatic substitute connection of an external functional means such as, for example, a blood cassette, in connection with a dialysis treatment. Furthermore, this arrangement may also be employed for an automatic hemofilter/dialysate connection of current and/or future cassette dialysis systems.

A second embodiment represents an automatically connecting arrangement between a first external functional means and a second external functional means.

In contrast to the first embodiment where the connection means of the invention is part of a treatment apparatus, the connection means of the invention is here chiefly realized as a single-use part arrangement on an external functional means.

The like arrangements may, for example, be employed as an automatic connection system for any bag treatment liquids for the treatment cassette in acute hemodialysis machines and in peritoneal dialysis machines of future generations.

A third embodiment encompasses manually connectable arrangements between an external functional means and a treatment apparatus.

In a like arrangement, the drive mechanism for automatic or automated connection of the two fluid-conducting systems may be omitted or be replaced with a similar manually operated system having, for example, the form of a lever for driving the mechanism.

In addition, when only one connection pipe each of an external functional means that is freely movable in three dimensions, i.e., a disposable connector (such as a connector on a tube), is coupled to the treatment apparatus, a part of the tolerance compensation system may be omitted (pivotal arrangement and pre-centering of the connection means).

The like arrangements may, for example, be employed for a rinse connection and/or substituate connection in dialysis treatment apparatuses involving tube systems, rinse connection in current blood cassettes, etc.

A fourth embodiment encompasses manual-connection arrangements between at least two external functional means.

In order to render the connection forces manageable by manual operation, additional force-enhancing construction elements such as eccentric levers and/or swivel nuts, etc. may be provided additionally. In such arrangements the use of resilient and/or easily sliding single-use part materials may be reasonable.

BRIEF DESCRIPTION OF THE DRAWINGS

In the following, the present invention shall be described by way of respective examples while making reference to the appended drawings. In the drawings, identical reference numerals designate same or identical elements, wherein.

DETAILED DESCRIPTION OF THE DRAWINGS

In the following, the invention shall be explained by making reference to a treatment apparatus, wherein the invention or its realization is not restricted to a treatment apparatus. However, anything said in connection with a treatment apparatus thus generally applies to medical-technical apparatuses such as, e.g., in therapy, diagnosis, analysis, etc. as well.

Figure 1:
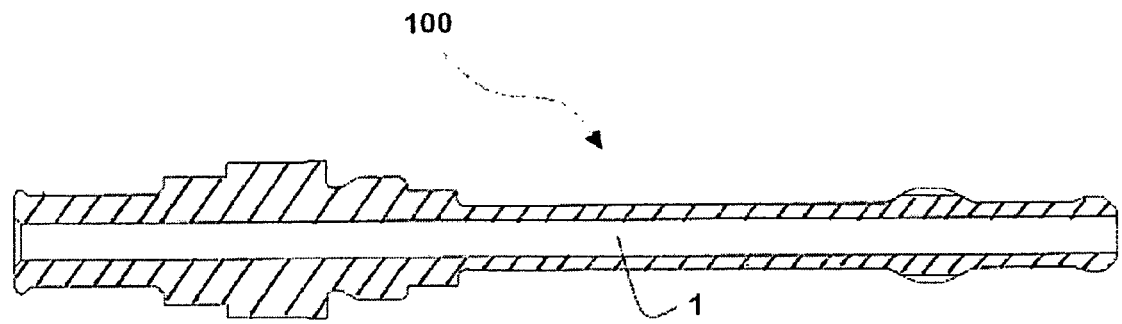
FIG. 1 shows a connection means of the invention in a longitudinal sectional view.

FIG. 1 shows a connection means 100 of the invention in a longitudinal sectional view.

The connection means 100 comprises an inner pipe 1 which is arranged—only in a preferred manner concentrically—inside an outer pipe 3. The inner pipe 1 may be axially displaceable in the outer pipe 3.

Figure 2:
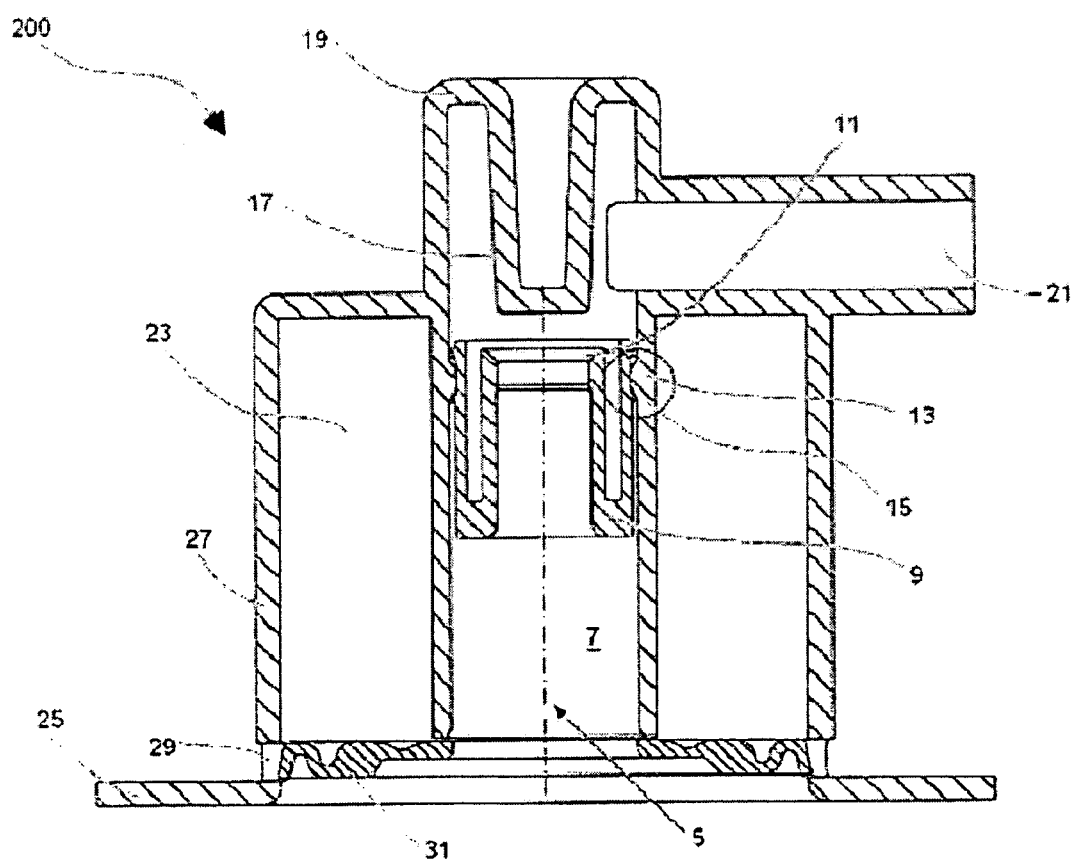
FIG. 2 shows a basic position of a connector subassembly of an external functional means in a longitudinal sectional view.
Figure 3:
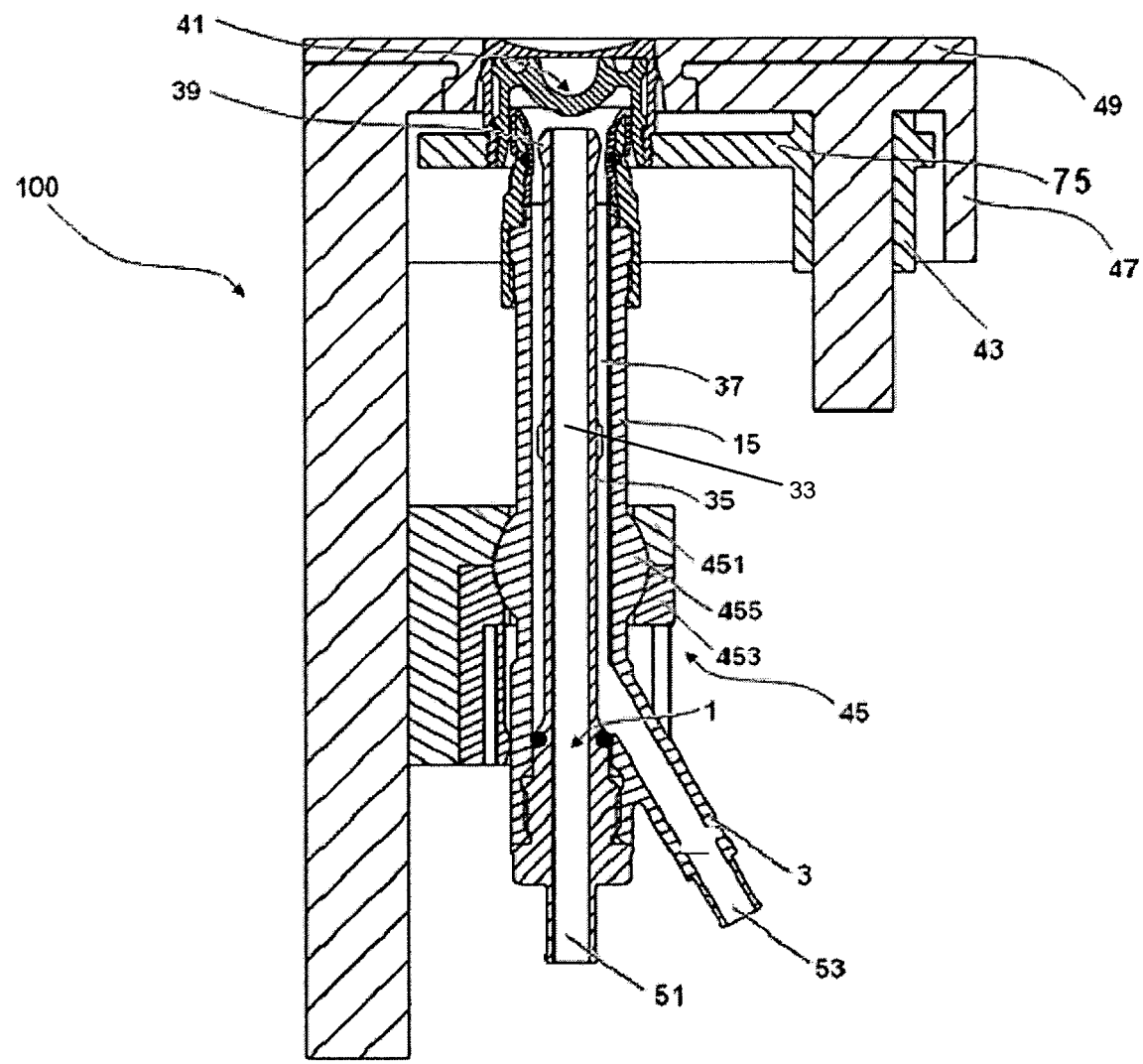
FIG. 3 shows a basic position of a connection means of the invention in a longitudinal sectional view.
Figure 4:
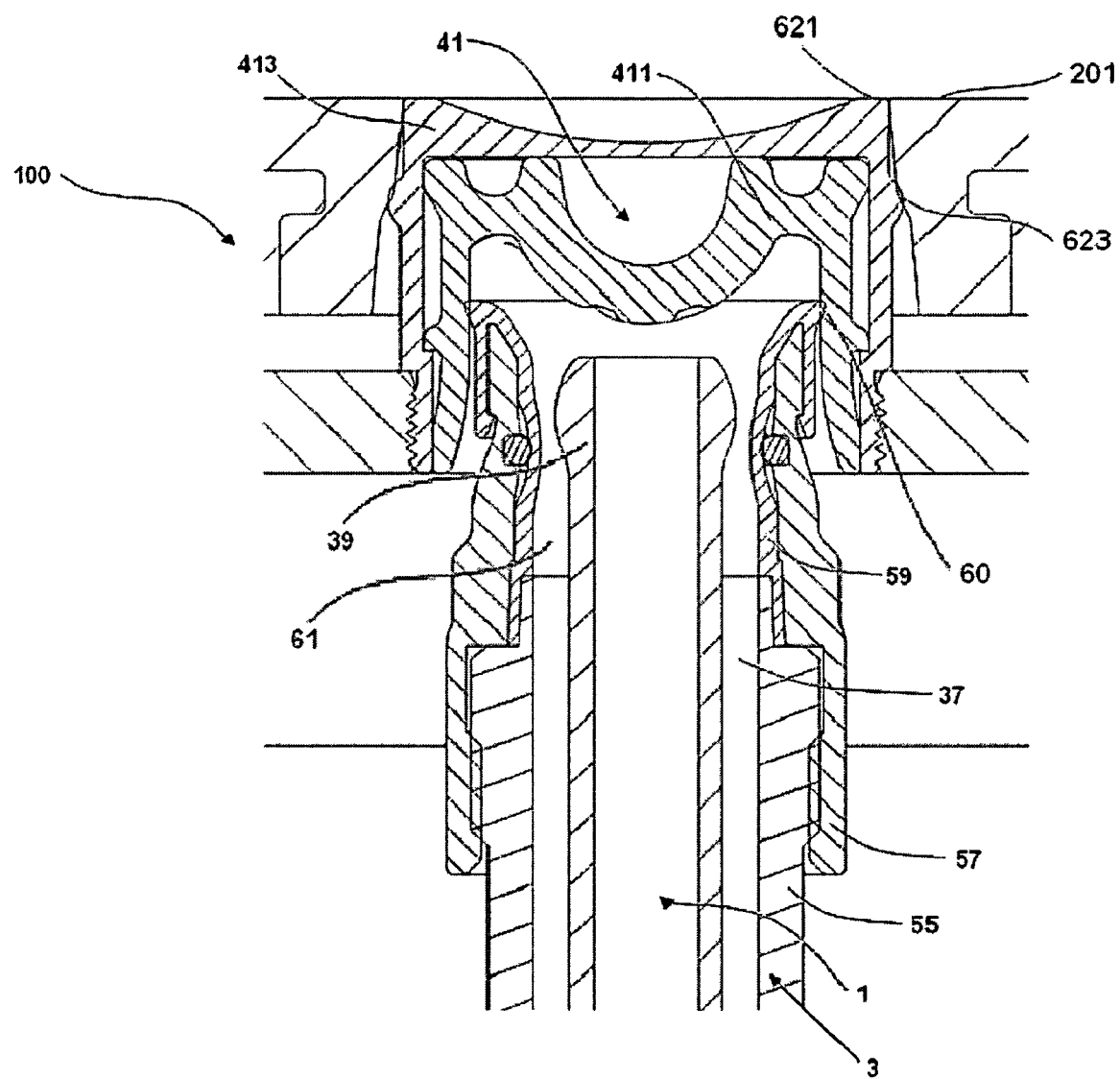
FIG. 4 shows an enlarged portion of the connection means of FIG. 3.

FIGS. 2 to 4 each show a basic position of arrangements or subassemblies, respectively, which are prepared for establishing a fluid connection in accordance with the method of the invention or with the aid of the connection means of the invention.

FIG. 2 shows a longitudinal sectional view of a connector subassembly 200 for the connection to a connection means of the invention which is not shown in FIG. 2.

Here, the connector subassembly 200 is part of an external functional means, while the connection means is part of a treatment apparatus. The connector subassembly 200 might, however, also be present on the treatment apparatus, with the connection means in turn being present on the external functional means. The connector subassembly 200 comprises a connection pipe 5 having an inner lumen 7. Inside the connection pipe 5 a closure sleeve 9 is arranged. The closure sleeve 9 comprises a closure collar 11 at its upper end (relative to its orientation in FIG. 2).

By a latching arrangement 13 in an inner wall 15 of the connection pipe 5 the closure sleeve 9 is retained in its position against a displacement, e.g. in a downward direction. The latching arrangement 13 comprises a thickening in the inner wall 15 of the connection pipe 5 and a recess or depression in a side wall of the closure sleeve 9. The invention does, however, also encompass reversed arrangements, i.e., depression in the inner wall and thickening in the closure sleeve. The disclosure of such "reversed" configurations is always inherent in the framework of the presently described invention whenever it is recognizable to the skilled person that they are technically practicable. As an alternative, the latching arrangement 13 might also be configured as a clamping means (not represented) or the like.

At its upper end (relative to the orientation in FIG. 2) the connection pipe 5 comprises a closure neck 17. In accordance with the representation in FIG. 2, the closure neck 17 has a crenellated shape. On the upper side of the closure neck 17 a support dome 19 is provided. On the right-hand side of the closure neck 17 (relative to the arrangement in FIG. 2) a passage 21 is provided. The passage 21 may lead to an interior of the external functional means. The connector subassembly 200 comprises a reception space 23 for receiving fluids. On its lower side (relative to the arrangement in FIG. 2) the connector subassembly 200 comprises a support ring 25. Between an outer wall 27 of the connector subassembly 200 and the support ring 25 a latching arrangement 29 for a touch-prevention panel 31 is provided.

FIG. 3 schematically shows a connection means 100 in accordance with the present invention in a longitudinal sectional view. Here, the connection means 100 is shown in its overall arrangement as part of a treatment apparatus. The connection means 100 comprises an inner pipe 1 as well as an outer pipe 3. The inner pipe 1 has been introduced into the outer pipe 3.

The inner pipe 1 comprises an inner lumen 33. Between the outer wall 35 of the inner pipe 1 and the inner wall 15 of the outer pipe 3, there is a gap presently designated as an outer lumen 37 of the inner pipe 1. Both the inner lumen 33 of the inner pipe 1 and the outer lumen 37 of the inner pipe 1 are suited for receiving fluids. At its upper end (relative to the orientation in FIG. 3) a wall of the inner pipe 1 comprises a widening 39. The widening 39 has a spherical configuration. As an alternative, both the entire inner pipe 1 and also its inner lumen 33 might comprise such a widening.

The connection means 100 is covered or closed by a rinsing cap 41. In order to be able to remove the rinsing cap 41 in an automated manner from the connection means 100 or vice versa, for example in order to establish a fluid communication with another fluid-conducting system, a drive mechanism may be provided. In FIG. 3 parts of such a drive mechanism having the form of a rinsing cap pivotal drive mechanism 43 are shown.

The rinsing cap pivotal drive mechanism 43 comprises a support means 45. The support means 45 comprises an upper part 451 and a lower part 453. The upper part 451 and the lower part 453 are fixedly connected to each other. In the basic position of FIG. 3, the upper part 451 and the lower part 453 are aligned substantially in parallel or in a mirror-symmetrical manner relative to each other. The upper part 451 and the lower part 453 together form a support (="carriage") that is not part of the pivotal drive mechanism. Inside the support, the outer pipe is mounted so as to be pivotable relative to the support within narrow limits, by means of a spherical or peripherally convex curvature in a corresponding "socket" of the support for the purpose of tolerance compensation. The support means 45 comprises a pivotal mount 455. The support means 45 is moved by means of a linear drive (not shown).

Furthermore, in FIG. 3, a chassis 47 of the treatment apparatus is shown. The chassis 47 comprises a rubber plate 49 on its upper side (relative to the orientation in FIG. 3) as well as on an inner side of the chassis 47 facing the rinsing cap 41. The inner pipe 1 comprises a fluid port 51 for introducing fluids into the inner lumen 33 of the inner pipe 1. The outer pipe 3 comprises a fluid port 53 for introducing fluids into the outer lumen 37 of the inner pipe 1 or for discharging the fluids therefrom.

FIG. 4 shows a portion of the connection means 100 of the invention of FIG. 3 in an enlarged representation. The portion or detail of the connection means 100 shown in FIG. 4 serves for establishing a connection in fluid communication of the treatment apparatus and of an external functional means.

The outer pipe 3 comprises a base body 55. The outer pipe 3 comprises a head cover or head body 57. The outer pipe 3 moreover comprises a sealing cover or sealing body 59. Between the widening 39 of the inner pipe 1 and the head body 57 of the outer pipe 3 opening upwardly—as shown in FIG. 4—in a trumpet shape there is a gap 61. The gap 61 may be a gap circling the inner pipe 1. It may have identical dimensions in every portion of its extension. It may, however, also have different dimensions in portions thereof if the inner pipe 1 were not arranged centrally in the outer pipe 3. The gap 61 is delimited laterally, or in a radial direction, by the sealing body 59 of the outer pipe 3. Below the gap 61 there continues the outer lumen 37 of the inner pipe 1 that is accessible to fluids.

The rinsing cap 41 comprises a fluid insert 411 as well as a mounting body 413. In accordance with the representation in FIG. 4, the rinsing cap 41 is placed on or over the sealing body 59 of the outer pipe 3, or applied over the inner pipe 1 and the outer pipe 3. The sealing body 59 of the outer pipe 3 is compressed at the seal 60 with the rinsing cap 41. The rinsing cap 41 or the fluid insert 411 thereof is expanded at the seal 60. The rinsing cap 41 is sealed against the treatment apparatus or a treatment apparatus front, respectively, at two peripheral seals 621 and 623. The rinsing cap 41 is seated flush in or on a surface 201 of the treatment apparatus.

Figure 5:
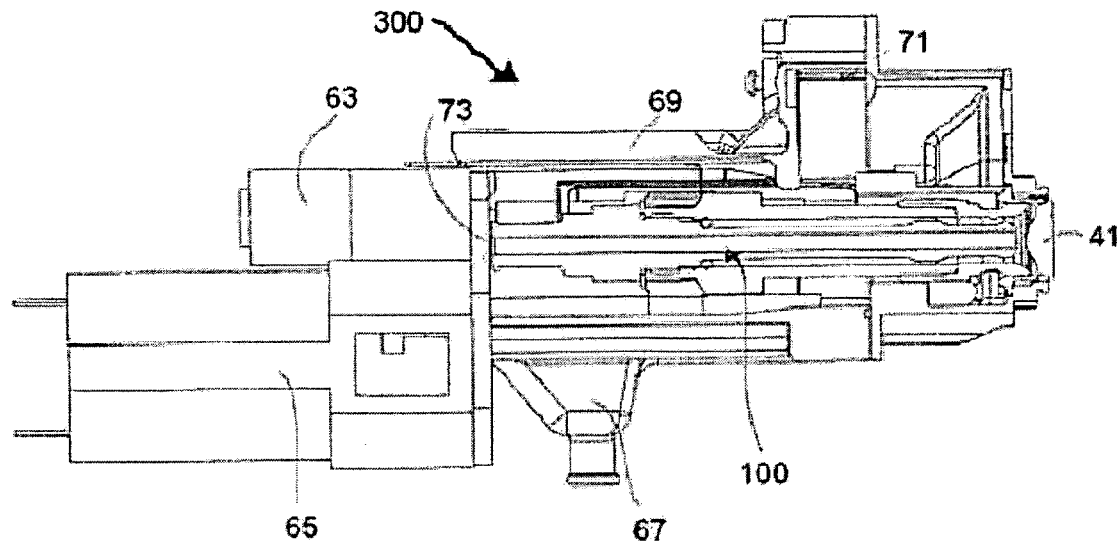
FIG. 5 shows a connection means of the invention in a partial longitudinal sectional view.

FIG. 5 schematically shows a connection means 100 of the invention as a part of a treatment apparatus 300 in a partial longitudinal sectional view. In its basic position shown in FIG. 5, the connection means 100 carries the rinsing cap 41. The treatment apparatus 300 comprises a motor, e.g. a DC motor 63, for pivoting the rinsing cap 41. The treatment apparatus 300 comprises a motor, e.g. a DC motor 65, for displacing the connection means 100. The treatment apparatus 300 comprises a dripping water drain 67. The treatment apparatus 300 comprises a film potentiometer 69 for recognizing a position of the connection means 100. In order to recognize a position of the rinsing cap 41, the treatment apparatus 300 may comprise several sensors which may in a given case also be of different kinds. As is shown in FIG. 5, the treatment apparatus 300 comprises a Hall sensor 71 for this purpose. An inlet 73 for introducing fluids into the connection means 100 leads to the interior of the connection means 100.

Figure 6:
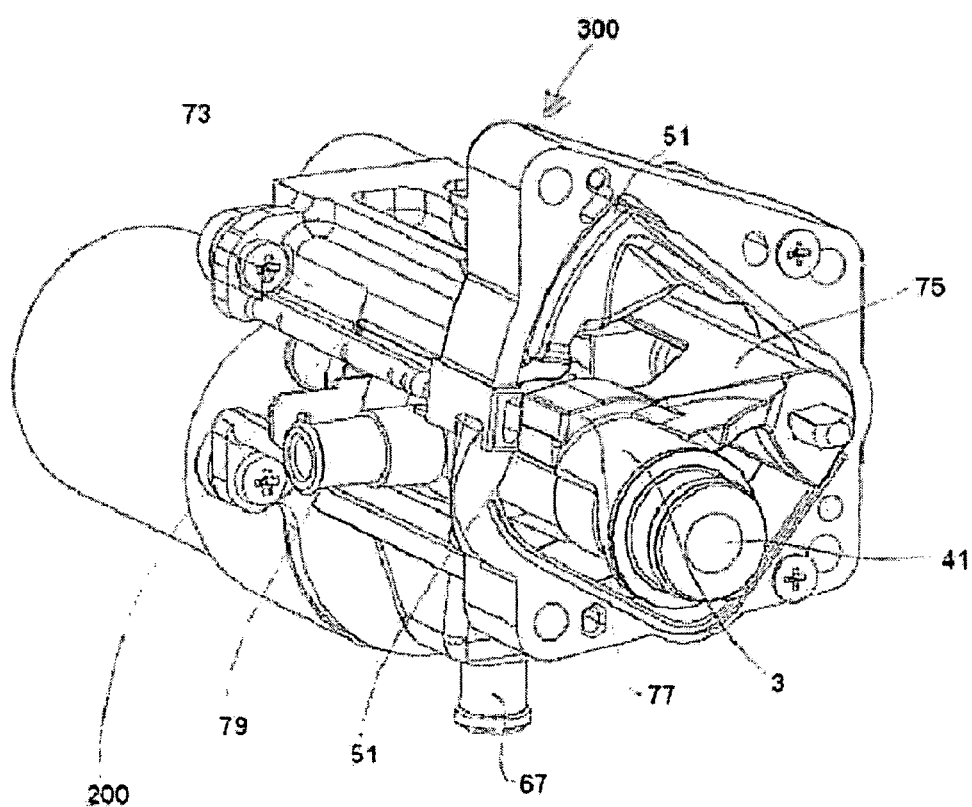
FIG. 6 shows a perspective view of the connection means of the invention as part of a treatment apparatus.

FIG. 6 shows the connection means 100 of the invention as a part of a treatment apparatus 300 from the front and above, as viewed from the side of the external functional means to be coupled or integrated. In the representation of FIG. 6, a front housing part of the treatment apparatus 300 has been removed. The connection means comprises the rinsing cap 41. The inlet 73 is concealed in the present representation of the connection means 100 of the invention. Indication of the reference numeral has the purpose of indicating its position. The treatment apparatus 300 comprises a pivoting lever 75. The rinsing cap 41 is rigidly connected to the pivoting lever 75. The pivoting lever 75 comprises a magnet 77. In FIG. 6 the treatment apparatus 300 is shown with two Hall sensors 51. The connection means 100 is provided with a pipe connection for a passage (not shown here) towards the external functional means. This passage may serve, for example, as a return line 79 for fluids.

Figure 7:
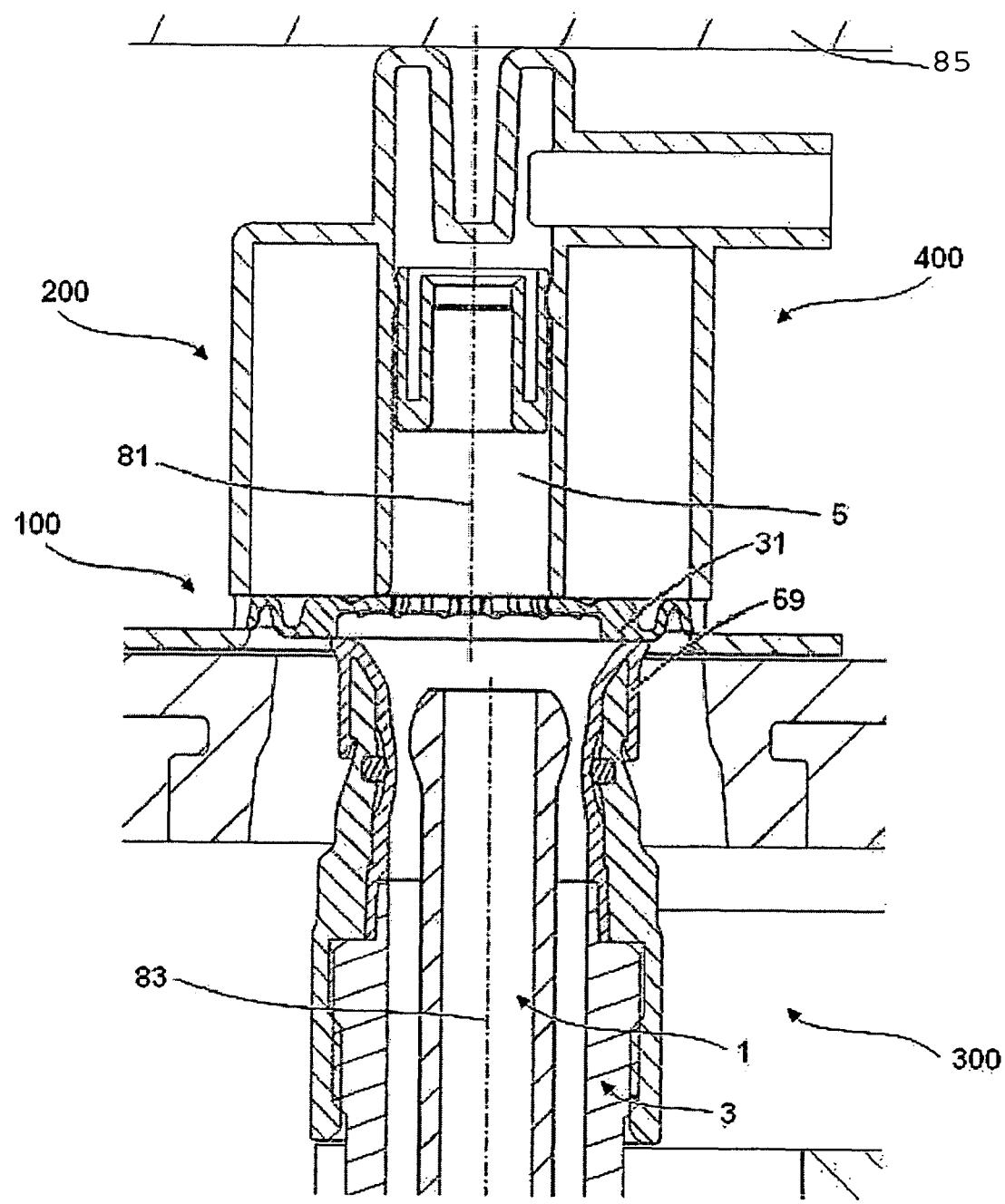
FIG. 7 shows a state in the course of establishing a fluid communication between an external functional means and a treatment apparatus with the aid of the connection means of the invention.

FIG. 7 schematically shows a state in the course of establishing a fluid communication between a treatment apparatus 300 and an external functional means 400 with the aid of the connection means of the invention 100. The arrangement is represented in a longitudinal sectional view.

In FIG. 7, the external functional means 400 has just been docked on to the treatment apparatus 300. FIG. 7 shows, as it were, the first contact between the treatment apparatus 300 and the external functional means 400 in the course of establishing the fluid connection.

The sealing body 59 of the outer pipe 3 abuts against the touch-prevention panel 31 of the connector subassembly 200 of the external functional means 400. A center axis 81 of the connection pipe 5 and a center axis 83 of the inner pipe 1 are positioned at a discernible offset. Therefore, the connection pipe 5 is not yet in the desired or aspired position relative to the inner pipe 1 for establishing the fluid communication.

Above the connector subassembly 200 or above the external functional means 400 in FIG. 7, a cover means 85 is provided, for example a door surface or panel.

Such a cover means may be employed, for instance, for pressing the external functional means in the treatment apparatus as disclosed, for example, in the German patent application No. 10 2009 012 633.3 (representative's file FM19A24) having the title "Vorrichtung zum Verbinden einer externen Funktionseinrichtung mit einer Anordnung, Anordnung aufweisend eine solche Vorrichtung and Verfahren zum Verbinden" [Device for connecting an external functional means to an arrangement, arrangement including a like device, and connecting method] deposited by the applicant of the present application with the German Patent and Trademark Office on Mar. 8, 2009, the relevant disclosure of which is herewith fully incorporated by way of reference.

Figure 8:
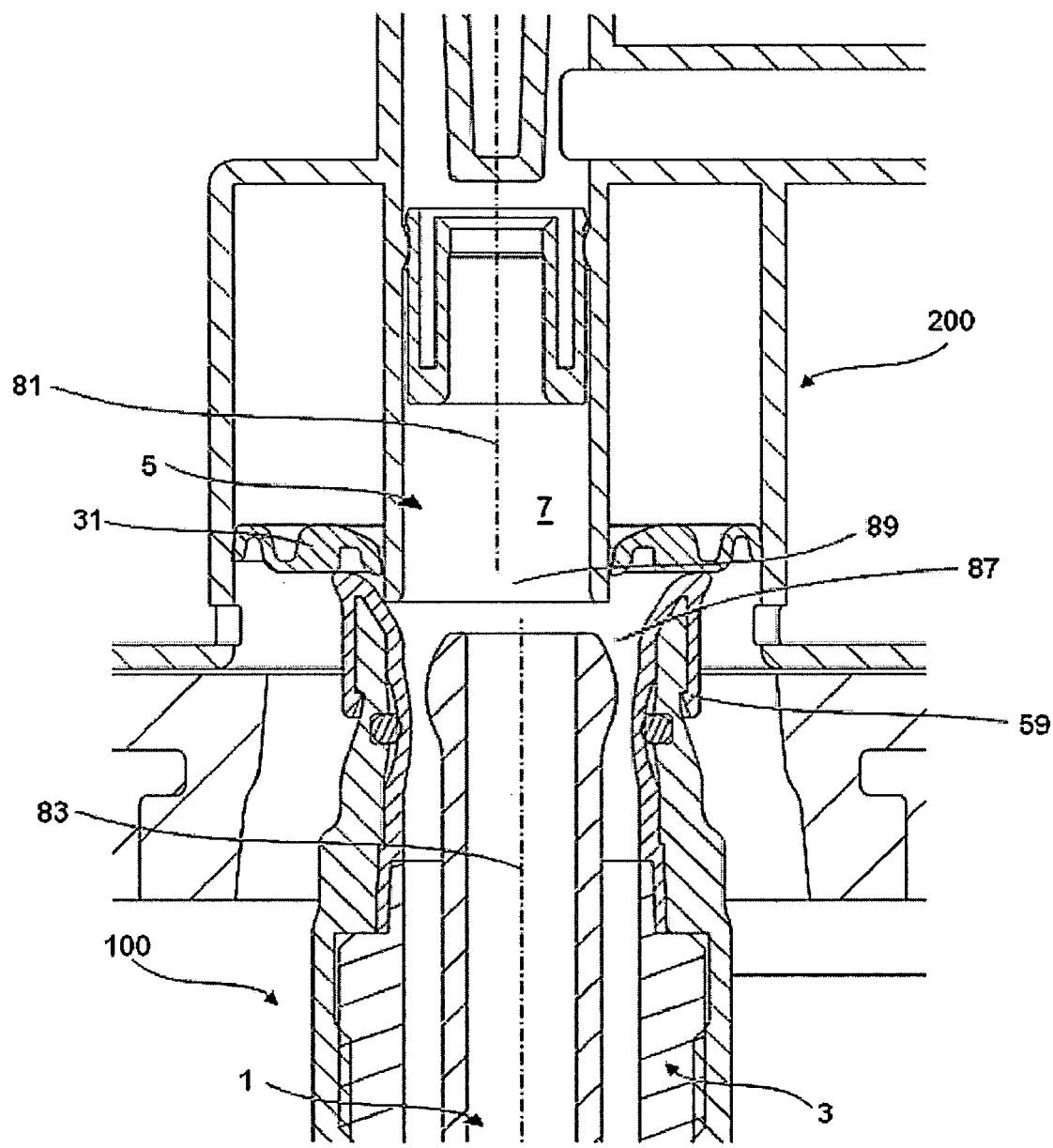
FIG. 8 shows the connection means of the invention in a first state in the course of establishing a fluid communication in a longitudinal sectional view.

FIG. 8 schematically shows a longitudinal sectional view of the connection means 100 at the beginning of threading the connection pipe 5 in the outer pipe 3. The outer pipe 3 comprises a leading-in funnel or guiding funnel 87. The guiding funnel 87 is part of the sealing body 59 of the outer pipe 3. In accordance with the representation in FIG. 8, the center axis 81 of the connection pipe 5 does not have a central alignment relative to the outer pipe 3. It may rather be seen that the outer pipe 3 is shifted to the right along the lower side of the connector subassembly 200, or vice versa. The guiding funnel 87 of the outer pipe 3 is contiguous or abuts against the touch-prevention panel 31 of the connector subassembly 200. The position of the center axis 83 of the inner pipe 1 is at an offset from the center axis 81 of the connection pipe 5. The connection pipe 5 has a lateral tolerance 89 in its inner lumen 7. The lateral tolerance 89 preferably serves for providing a certain measure of play, for example in order to compensate inaccuracies of fit. The lateral tolerance 89 advantageously allows to perform threading of the inner pipe 1 in the connection pipe 5 in an easy manner and/or free from damage.

Figure 9:
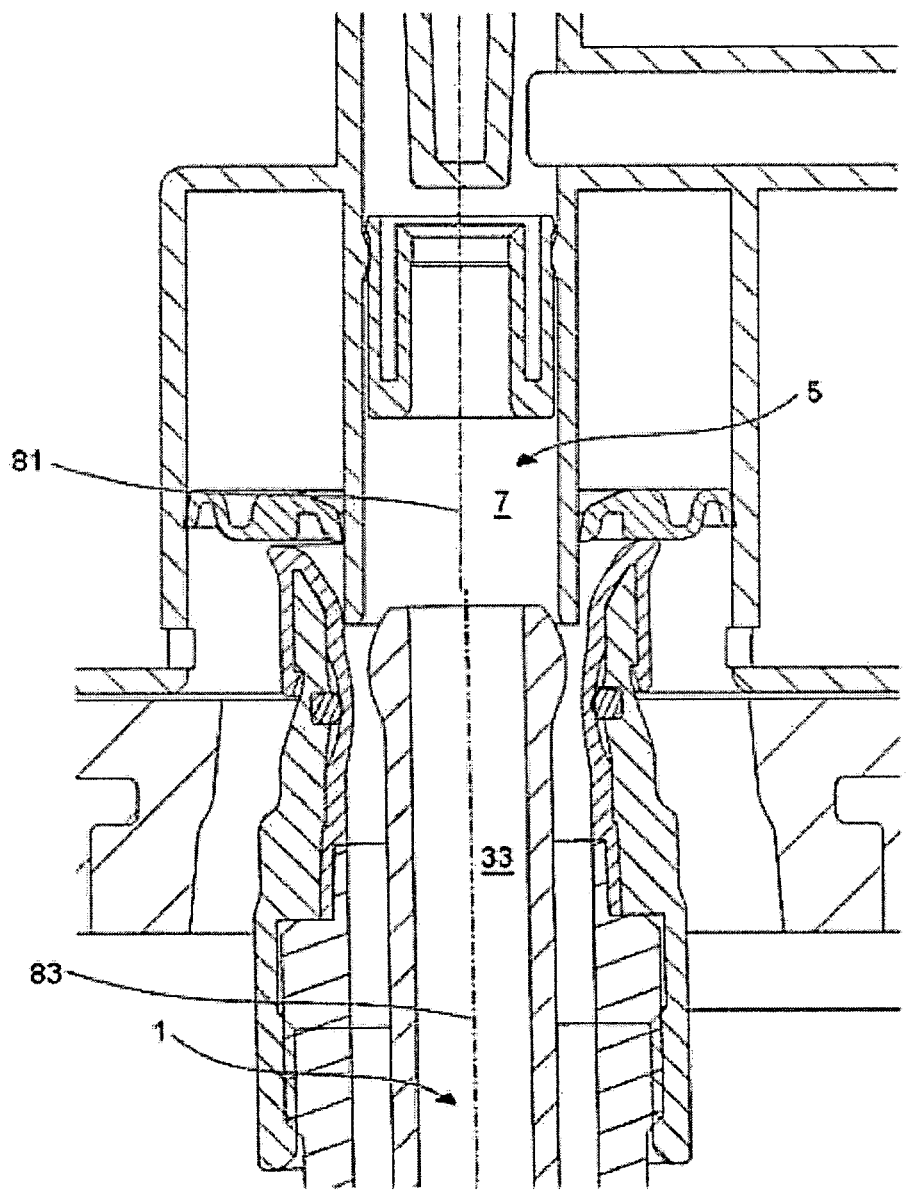
FIG. 9 shows the connection means of the invention in a second state in the course of establishing the fluid communication in a longitudinal sectional view.

FIG. 9 schematically shows a longitudinal sectional view of the connection means 100 at the end of threading the outer pipe 3. The inner pipe 1 is partly inserted or introduced into the connection pipe 5 (or vice versa). The inner lumen 33 of the inner pipe 1 is in fluid communication with the inner lumen 7 of the connection pipe 5. The preferred arrangement for fluid connection has, however, not been reached yet. In accordance with the representation in FIG. 9, the inner pipe 1 is not properly aligned yet with the connection pipe 5. The center axis 83 of the inner pipe 1 and the center axis 81 of the connection pipe 5 are offset relative to each other.

Figure 10:
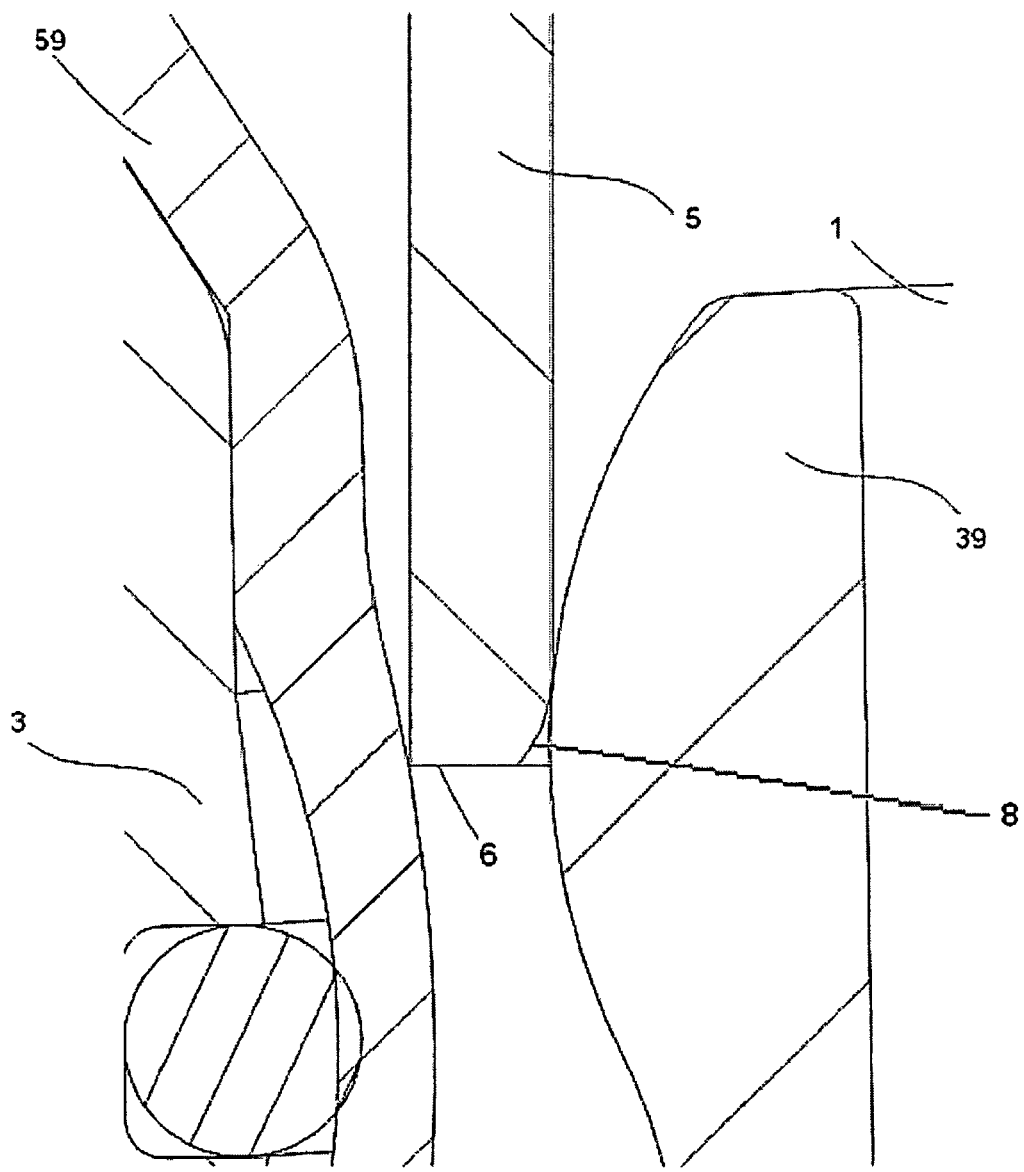
FIG. 10 shows an enlarged portion of the connection means of the invention in a third state in the course of establishing the fluid communication.

FIG. 10 shows an enlarged detail representation of a position at the beginning of threading the inner pipe 1 in the connection pipe 5. During threading the inner pipe 1 in the connection pipe 5, the wall of the connection pipe 5 is pushed between the widening 39 of the inner pipe 1 and the sealing body 59 of the outer pipe 3.

Figure 11:
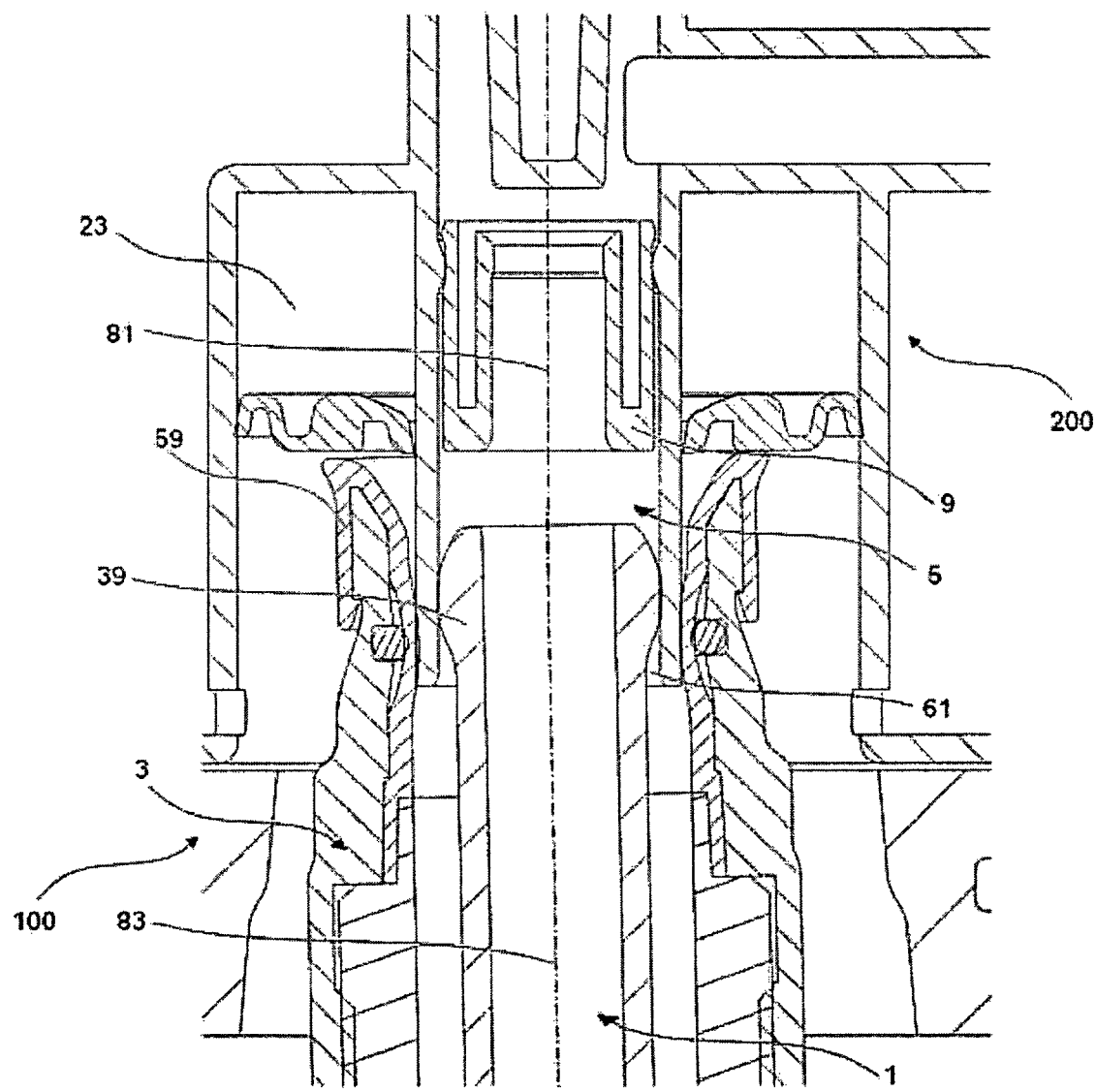
FIG. 11 shows the connection means of the invention in a fourth state in the course of establishing the fluid communication in a longitudinal sectional view.

FIG. 11 schematically shows the connection means 100 in a position of minimum connection of the inner pipe 1 with the connection pipe 5. The inner pipe 1 is inserted into the connection pipe 5 with the widening 39 and beyond. The wall of the connection pipe 5 substantially fills the gap 61 between the sealing body 59 of the outer pipe 3 and the widening 39 of the inner pipe 1. The center axis 81 of the connection pipe 5 and the center axis 83 of the inner pipe 1 are now coincident. As a result of telescoping the inner pipe 1, the connection pipe 5 and the outer pipe 3, the widening 39 pushes the connection pipe 5 apart or expands it at least locally. The sealing body 59 of the outer pipe 3 presses or pushes from the outside against the wall of the connection pipe 5. The sealing body 59 of the outer pipe 3 pushes the touch-prevention panel 31 of the connector subassembly 200 in an upward direction in FIG. 11, whereby the reception space 23 of the connector subassembly 200 becomes smaller, for example in comparison with the reception space shown in FIG. 2.

Figure 12:
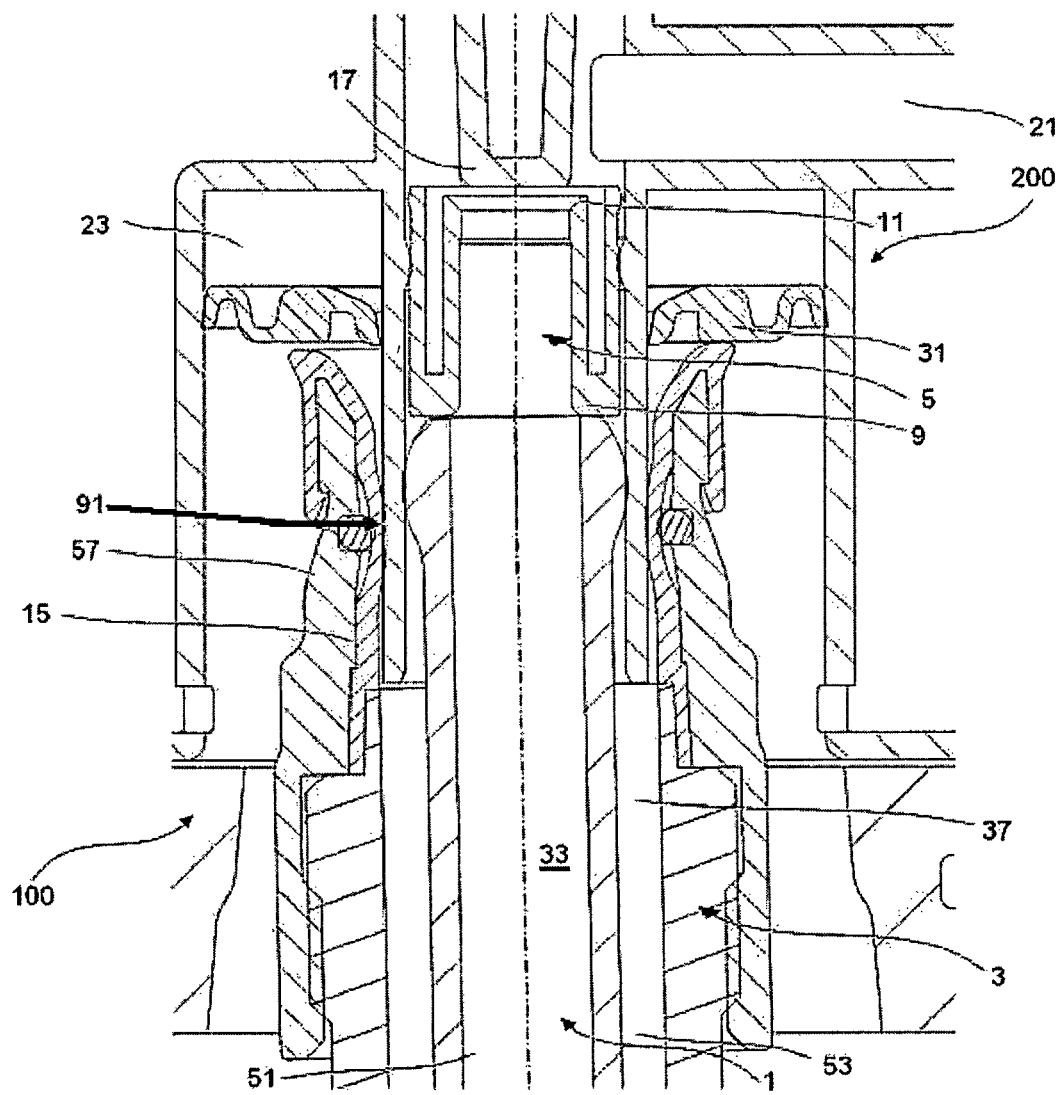
FIG. 12 shows the connection means of the invention in a fifth state in the course of establishing the fluid communication in a longitudinal sectional view.

FIG. 12 schematically shows the connection means 100 in a position of maximum connection of the inner pipe 1 and the connection pipe 5. Between the positions of minimum connection and maximum connection any axial position is admissible. This advantageously results from the axial tolerance compensation provided with the connection means of the invention. In the maximum connection position, or position of maximum connection as shown in FIG. 12, the inner pipe 1 is shifted even further into the connection pipe 5 as compared with the position of FIG. 11. The widening 39 is located completely inside the connection pipe 5.

In FIG. 12, the touch-prevention panel 31 has been shifted further in an upward direction, so that the reception space 23 has become even smaller in comparison with the reception space of FIG. 11. The end side of the widening 39 is directly contiguous with the closure sleeve 9 of the connector subassembly 200 even before the condition of maximum connection is reached, and thus displaces the closure sleeve 9 in an axial direction. The closure collar 11 is contiguous with the closure neck 17 of the connector subassembly 200.

The fluidic connection and/or seal may be effected by insertion of the inner pipe 1 having the widening 39 into the connection pipe 5. As the outer diameter of the widening 39 is larger than the inner diameter of the connection pipe 5, the connection pipe 5 is widened or expanded annularly in the location of largest diameter of the widening 39. This may advantageously result in the creation of an annular sealing zone in which the inner wall of the connection pipe 5 is applied to the outer circumference of the largest outer diameter of the widening 39 under—preferably elastic—tensioning of material.

In combination with a sufficiently low roughness of the associated surfaces, such tensioning of material due to expansion may ensure a sufficient fluid-tightness of the connection against the specified differential pressures relative to the environment.

The inner wall of the connection pipe 5 preferably has a cylindrical configuration. Relative to the diameter of the connection pipe 5, the inner wall of the connection pipe 5 may preferably be realized with thin walls and/or a constant wall thickness. In this way, it may advantageously be possible to keep the expanding and/or sealing effect constant at any distance of insertion of the inner pipe 1 into the connection pipe 5.

As a material for the connection pipe 5 and/or the inner pipe 1 and/or the outer pipe 3, thermoplastic materials such as polypropylene, polyamide, polycarbonate, thermoplastic composite materials including PTFE (polytetrafluoroethylene) and the like may be employed, however, without being restricted thereto. These materials may advantageously be processed at low cost by means of injection molding techniques. They may moreover possess a favorable rigidity and/or tenacity for the above-described principle of sealing involving expansion.

Typical dimensions of the connection pipe 5 encompass an inner diameter of 4 mm to 8 mm, a wall thickness of 0.4 mm to 1 mm, as well as a length of 20 mm to 40 mm.

In general, due to its geometry a pipe predominantly has a lower expansion stiffness in the vicinity of its open mouth and/or predominantly has a higher expansion stiffness in the vicinity of the coupled end than in a central region.

For this reason, it is preferably possible in the course of establishing the fluid connection to use for the various connection positions those regions of the connection pipe 5 that have a distance from one or two ends of the connection pipe 5 of slightly more than one times the inner diameter.

Due to its preferably thin-walled and/or simple geometry, the connection pipe 5 preferably is the connection half-assembly or the system which is realized on the side of an external functional means 400, for instance in the form of a single-use part.

In the above-described manner, the widening 39 may produce a seal in the external functional means. The widening 39 may further provide tolerance compensation. The widening 39 of the inner pipe 1 preferably is realized such that at least the annular region of expansion has the form of a sphere. The center of the sphere may be situated on a center axis or axis of symmetry 83 of the inner pipe 1.

If the center axis or axis of symmetry 83 of the inner pipe 1 and the center axis or axis of symmetry 81 of the connection pipe 5 do not coincide, the same annular geometry of contact or sealing may thus always advantageously be effected in this way. In cases of particularly high demands to low connection forces and/or to particularly high sealing effects (such as sealing very thin fluids such as liquids and gases) it may be possible to realize the globularly spherical annular region of the widening 39 in form of several single, narrower annular sealing bars or in form of an elastomer ring insert.

Narrow annular sealing bars may advantageously provide redundant sealing ring zones having the same or elevated sealing pressure.

An elastomer ring insert may advantageously bridge or shunt out or equalize small roughnesses between the sealing mates.

The widening 39 of the inner pipe 1 may present a diameter overdimension relative to an inner diameter of the connection pipe 5. Such a diameter overdimension preferably is in a range from 2% to 10% of the inner diameter of the connection pipe 5. The inner pipe 1 having the widening 39 may be a connection half-assembly of the treatment apparatus 300.

Due to requirements such as capability of multiple use and/or disinfection with hot fluids (e.g. liquids), the connection means 100 or the inner pipe 1, respectively, and/or the widening 39 of the inner pipe 1 preferably comprise(s) materials such as stainless steel, titanium, steels having ceramic, oxide, and/or PTFE—(polytetrafluoroethylene-) containing coatings and/or injection-moldable sintered ceramics such as zirconium oxide or are made of such materials. It is, however, equally possible to realize the connection means 100 of the invention as single-use part, e.g. by using thermoplastic resins.

In particular with the use of widenings 39 having thin or narrow annular sealing bars and/or having an elastomer ring insert (superposition with negative widening) it may be possible to realize the connection half-assembly in a reverse manner, i.e., the connection pipe 5 as a stiff or non-deformable component of the treatment apparatus 300, or as a stiff or non-deformable component of the external functional means 400. This is in particular preferred when the realization of thin-walled connection pipes 5 is not possible or only possible at high complexity or costs.

The outer pipe 3 comprises a redundancy sealing bead 91 as an example of another redundant sealing security. Generally, contact between the outer wall of the connection pipe 5 and the inner wall 15 of the outer pipe 3 is established once a connection position is reached. The redundancy sealing bead 91 may serve for radially supporting the connection pipe 5.

The redundancy sealing bead 91 primarily has two purposes: Firstly, the redundancy sealing bead 91 serves for radially supporting the connection pipe 5 in order to maintain the expansion-type main seal in accordance with the invention. Secondly, the redundancy sealing bead 91 serves as a redundant secondary sealing. The O-ring shown in FIG. 12 on the left next to the redundancy sealing bead 91 serves as a spring. The redundancy sealing bead 91 may have an annular configuration.

FIG. 12 shows a typical connection position of the connection means of the invention for a redundancy sealing bead 91. In this position, the connection pipe 5 of the connector subassembly 200 is again pressed against the connection means 100 in an annular zone at the inner wall 15 of the outer pipe 3. A fluidic seal may exist.

The inner diameter of the redundancy sealing bead 91 attached to the outer pipe 3 may be selected to be about 2% to 10% smaller than the outer diameter of the substantially cylindrical and/or smooth-walled connection pipe 5.

At least one of the two sealing mates, the outer pipe 3 and/or the connection pipe 5, usually both of them, may preferably be realized to be elastic.

As a result of substantially axial telescoping of the connection pipe 5 in the outer pipe 3, a radial inward compression towards the connection pipe 5 or a radial outward expansion of the redundancy sealing bead 91 may be effected in the region of the redundancy sealing bead 91.

As in the case of the main seal, an annular zone may be created in which the connection pipe 5 is pressed against the redundancy sealing bead 91 under radial stress.

In this way, the tensioning of material in combination with a sufficient smoothness, or in combination with a sufficient assimilation of the associated surfaces, may advantageously result in fluid-tightness of the connection pipe 5 against the outer pipe 3.

The redundancy sealing bead 91 is preferably arranged in immediate vicinity of the widening 39 of the main seal at an axial offset of up to about one times the inner diameter of the connection pipe 5 in a direction towards the open pipe opening of the connection pipe 5.

In this way, a fatigue or tiredness of the expansion-type main seal as a result of the widening 39 may advantageously be counteracted by plastic deformation of the connection pipe 5.

The offset arrangement of the widening 39 may on the one hand ensure a continued elastic deformation capability of the connection pipe 5 both to the outside and to the inside. On the other hand, a pipe may have a general tendency to a funnel-type expansion towards the open pipe end due to being expanded. This type of expansion is advantageously also counteracted by the offset arrangement of the redundancy seal annular zone of the redundancy sealing bead 91.

The redundancy sealing bead 91—and likewise but independently of this the widening 39 as well—may be made of hard or include materials such as metals and/or ceramics, of resilient materials such as PTFE and/or POM (polyoxymethylene), and/or of elastomer materials such as, e.g., silicone rubber and the like.

In a particularly preferred manner, the redundancy sealing bead 91 represented in FIG. 12 is made of PTFE in one piece with the head body 57 of the outer pipe 3.

The PTFE material may be provided with persistent elasticity in a radial inward direction by tempering (cold stretching) and/or by being mounted against an elastic ring of elastomers and/or by means of annular springs.

Due to the preferred material PTFE having a low coefficient of friction, the axial pushing force required for sealing may advantageously be minimized.

The elastic elements may advantageously cause a constant sealing effect even in the event of an admissible wear of the PTFE layer.

By means of the connection means 100 of the invention, it is advantageously possible to obtain tightness monitoring and/or leakage protection.

In the connection position of FIG. 12, the connection pipe 5 is connected on the inside to the fluid port 51 of the inner pipe 1 in a fluid-tight manner. The connection pipe 5 is further fluid-tight against the fluid port 53 of the outer pipe 3.

For monitoring tightness, the following method may preferably be used: The inner lumen 33 of the inner pipe 1 preferably serves for the regular fluid connection. In or during the connection, the outer lumen 37 of the inner pipe 1 is optionally filled with gas, for example air, and/or liquid. The outer lumen 37 is preferably coupled to a conduit leading to the waste water branch, e.g., a dripping water drain (not shown in FIG. 12), via a pressure limiting valve.

The response pressure of the pressure limiting valve may be set to be lower than the maximum liquid pressure occurring in the inner fluid connection. The response pressure of the pressure limiting valve may furthermore be lower than the minimum sealing pressure against the environment that may be obtained by the redundancy sealing bead 91.

In a particularly preferred manner, the response pressure of the pressure limiting valve is even below the pressure of the atmosphere.

In the event of a leakage, the pressure limiting valve may eventually open and allow the leaked liquid to pass over into the waste water branch in a controlled manner. In this way it is advantageously possible to poll the switching condition of the pressure limiting valve and thus recognize a possible leakage of the main seal as soon as possible on behalf of the self-check routine prior to the beginning of the respective treatment method. In this way, it may in turn advantageously be possible to take countermeasures early on, such as replacing the external functional means 400 and/or replacing worn components of the treatment apparatus 300.

As an alternative to polling the switching condition of the pressure limiting valve, it is also possible to evaluate the signal of an additionally provided pressure sensor.

As an alternative, it may also be possible to apply a vacuum to the fluid port 53 of the outer pipe 3 (e.g., when using a fluid connection under negative pressure conditions) and/or a direct connection with the drain that is open to the atmosphere (e.g., when using a fluid connection under overpressure conditions) and to perform a pressure keeping test of the inner fluid connection—in particular between inner pipe 1 and connection pipe 5—on behalf of the self-check routine.

The monitoring method described first in the foregoing may advantageously be performed even prior to the beginning of the actual treatment or main treatment such as, for example, a dialysis treatment. It may advantageously also be effective continuously during the main treatment.

The monitoring method described second in the foregoing may be restricted to tightness monitoring prior to the beginning of the main treatment.

Both fluid arrangements may advantageously ensure that treatment fluids will not leak to the environment at any point of time. Instead, possibly occurring leakage fluids are discharged into the waste water branch of the treatment apparatus 300 in a controlled manner.

Figure 13:
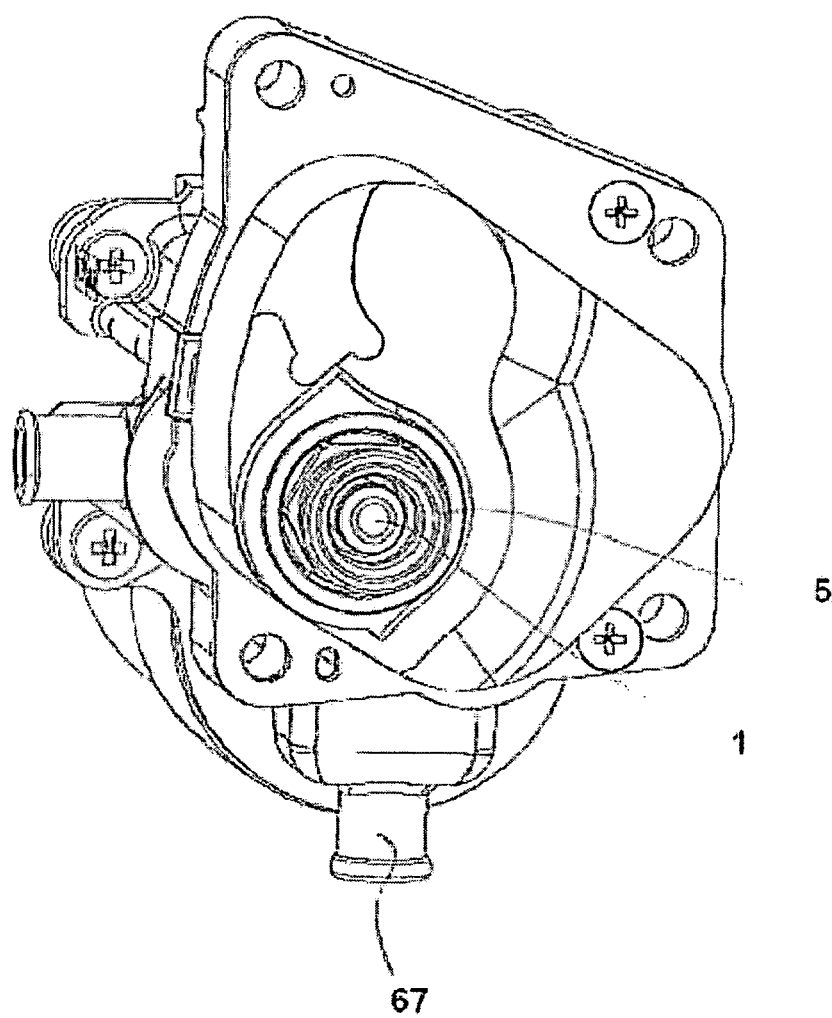
FIG. 13 shows another perspective view of the connection means of the invention as part of a treatment apparatus.

FIG. 13 is a view of a connection means 100 of the invention in a connection position.

Figure 14:
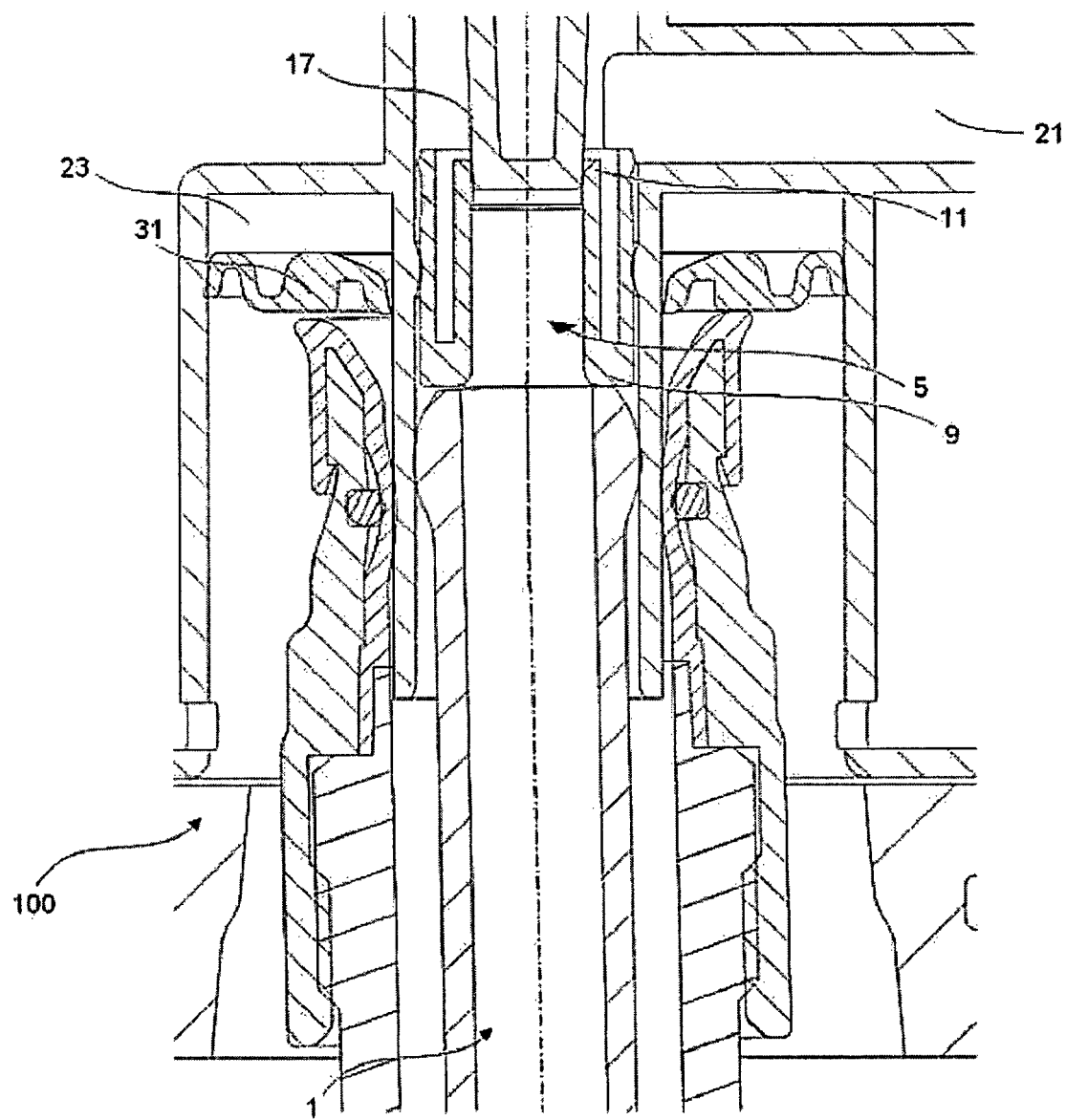
FIG. 14 shows the connection means of the invention in a first state of a fluid communication in a longitudinal sectional view.

FIG. 14 is a longitudinal sectional view of the connection means 100 of the invention in a closed position. A fluid communication between the inner pipe 1 and the connection pipe 5 has been established. The reception space 23 is further made smaller, e.g. in comparison with the one of FIG. 12, by sliding up the touch-prevention panel 31. The closure sleeve 9 is pushed by the closure collar 11 from below (relative to the arrangement in FIG. 14) into the closure neck 17. The closure sleeve 9 is displaced in an upward direction in FIG. 14 by displacing or shifting the connection means 100 into the closure position (with the rinsing cap being open). The closure sleeve 9 closes the passage 21 to the external functional means. Closing the external functional means may take place, for example, at the end of a treatment session.

Figure 15:
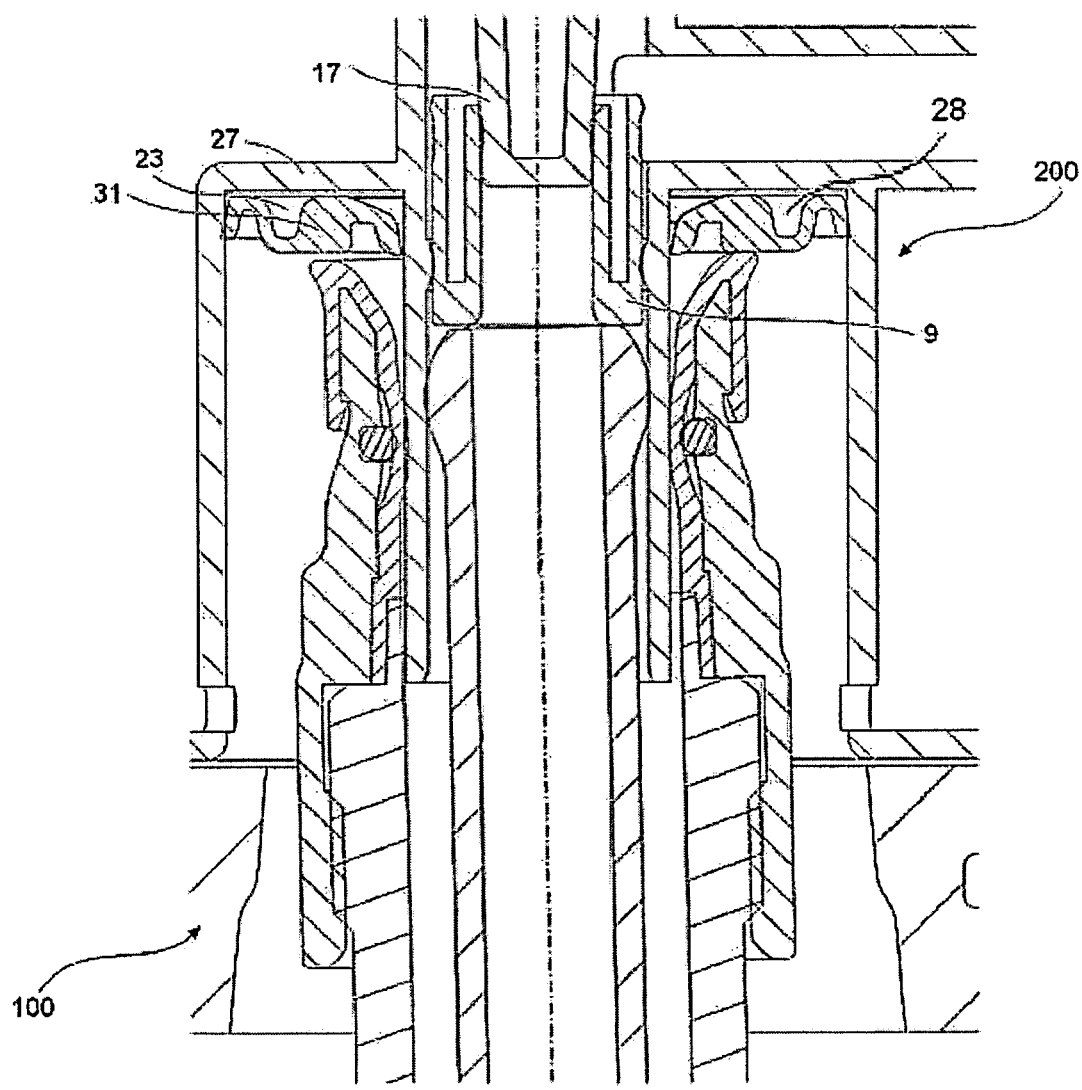
FIG. 15 shows the connection means of the invention in a second state of the fluid communication in a longitudinal sectional view.

FIG. 15 is a sectional view of the connection means 100 of the invention at a maximum admissible displacement of the closure position. A residual gap 28 preferably remains between the touch-prevention panel 31 and the inner side of the outer wall 27. This may advantageously contribute to safe and smooth operation. The reception space 23 has a minimum size. The closure sleeve 9 is again pushed further into the closure neck 17.

Figure 16:
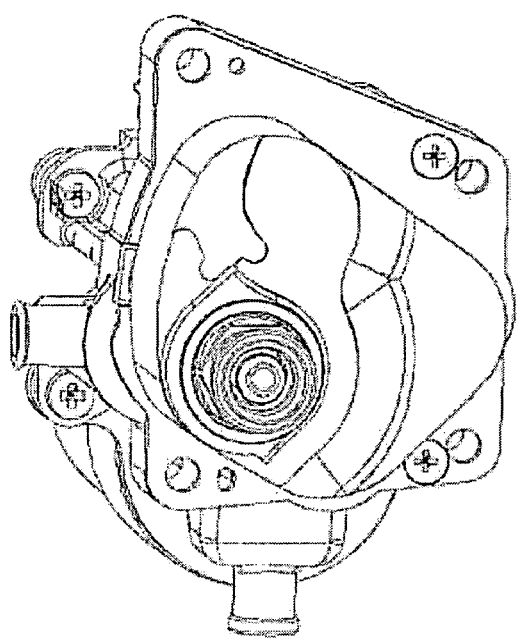
FIG. 16 shows another perspective view of the connection means of the invention as part of a treatment apparatus.

FIG. 16 is a view of a connection means 100 of the invention without a rinsing cap. In order to execute a cleaning program, for example, the connection means 100 may be taken from the closure position into a rinsing position. In order to displace the rinsing cap into the rinsing position, the support means or support is displaced axially against the connecting direction to such a distance that the rinsing cap may be pivoted above the connection means in an axially aligned manner. Upon completed pivoting movement, the support or the support means is displaced in the connecting direction until a sealing connection of the connection means to the rinsing cap is obtained.

Figure 17:
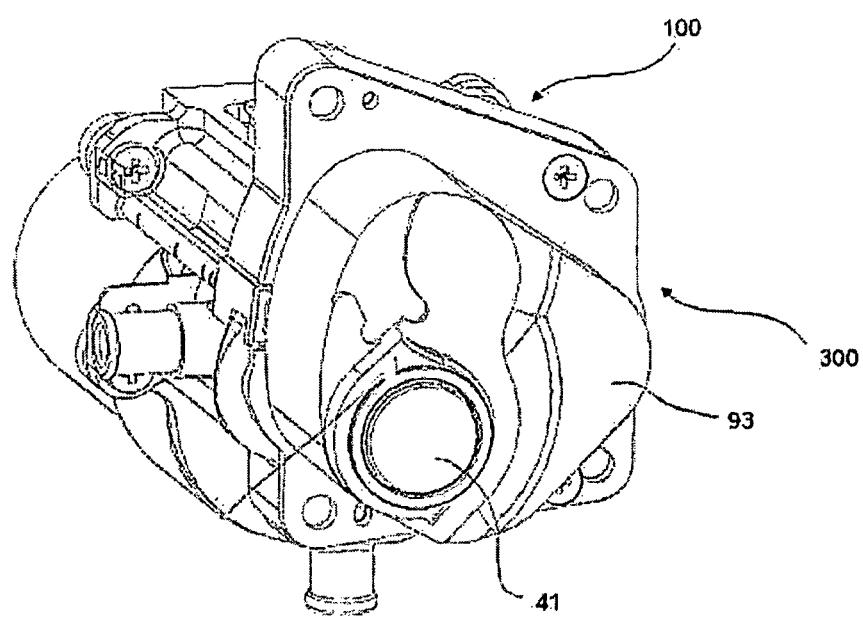
FIG. 17 shows another perspective view of the connection means of the invention as part of a treatment apparatus.
Figure 18:
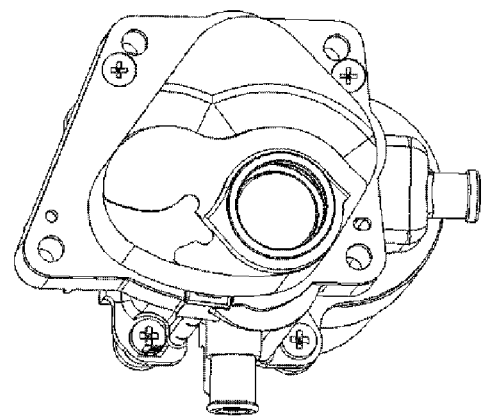
FIG. 18 shows a perspective view of a connection means of the invention in a pivoted position.
Figure 18:
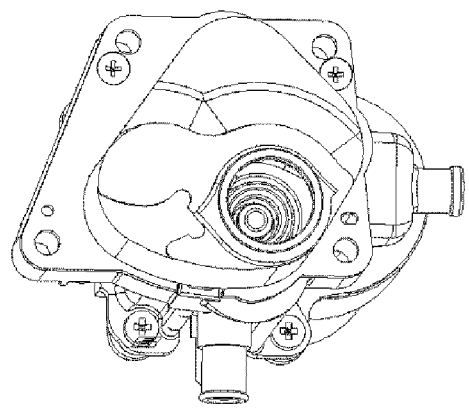
Figure 19A:
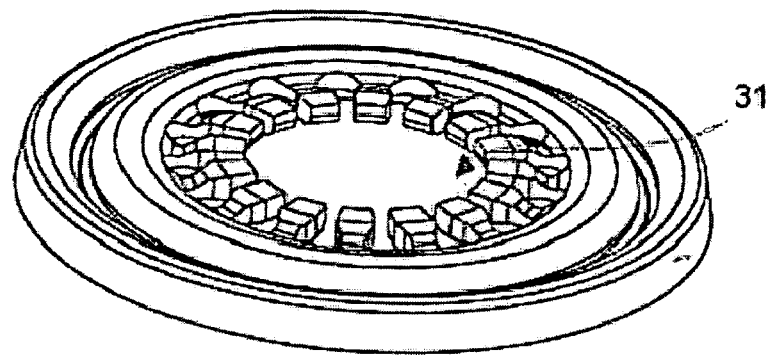
FIG. 19A shows the touch-prevention panel prior to use in a perspective view.
Figure 19B:
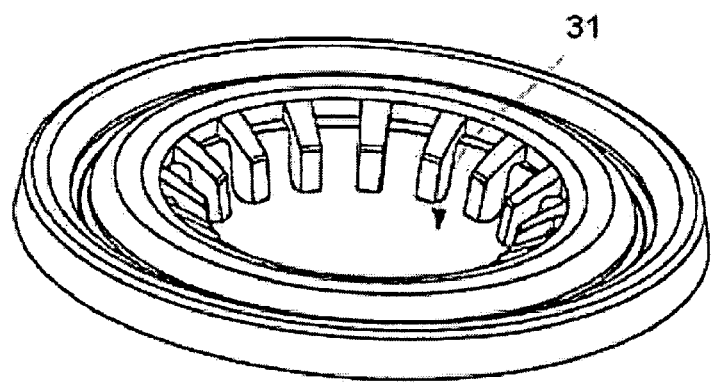
FIG. 19B shows the touch-prevention panel after use in a perspective view.

FIG. 17 is a view of a connection means 100 of the invention in a rinsing position. The housing front part 93 of the treatment apparatus 300 conceals components of the connection means 100 and/or of the treatment apparatus 300 situated behind it. Reference numerals of concealed elements shall be indicated in the following description in order to facilitate an understanding of their co-operation.

The rinsing position may correspond to the basic position of the connection means 100. In the rinsing position, the rinsing cap 41 has been pivoted in front of the opening (of the connection means 100) in the housing front part 93 of the treatment apparatus 300. In a preferred manner, the rinsing cap 41 is axially flush with the front side of an actor/sensor mat (not shown). A possibly existing ring gap between the rinsing cap 41 and the housing front part 93 of the treatment apparatus 300 may, for example, be sealed with an O-ring against penetrating fluids, in particular penetrating liquids.

The connection means 100 preferably plunges into the rinsing cap 41 such that the sealing body 59 of the outer pipe 3, or an outer edge thereof, is sealed against an outside in the rinsing cap 41.

When the sealing body of the outer pipe 3 is made of a composite PTFE material, it may represent the softer partner of this sealing pair. It may therefore preferably be configured such that it may advantageously be replaced without opening the treatment apparatus 300.

In order to clean the connection means 100, cleaning liquid is generally supplied through the inner pipe 1 and discharged through the outer pipe 3.

A Hall sensor, e.g. a H2Conn (S502), may detect the magnet 77 attached on the pivoting lever 75. In this way, the axial position of a spindle nut (and thus of the connection pipe 5 of the external functional means 400) may be determined with the aid of the potentiometer, e.g. the linear potentiometer SPosConn (S503). The axial position of the rinsing cap 41 may be determined based on the distance of the outer edge of the sealing body from the housing front part 93 of the treatment apparatus 300.

In order to pass over from the rinsing position into the connection position, the following sequence of movements may be executed: Initially, an axial movement of the connection means 100 together with the rinsing cap 41 against the connecting direction (to the left in FIG. 17) takes place. Subsequently, the connection means 100 is moved out of the rinsing cap 41 in the axial direction. The rinsing cap 41 may remain in its position. Then a pivoting movement of the rinsing cap 41 may take place to such an extent as to enable a free movement of the connection means 100 in the connecting direction. At last, the connection means 100 may be moved out of the front plane of the treatment apparatus 300 in an axial direction and into the external functional means 400.

In order to get from the rinsing position into the connection position, the connection means 100 may be displaced axially in the connecting direction. Due to the pivoting lever 75 pivoted open, the rinsing cap 41 preferably exposes an opening in the housing front part 93. The connection means 100 may be displaced in a forward direction. The connection means 100 may now penetrate into the connection pipe 5 of the connector subassembly 200 of the external functional means 400.

In the following, preferred embodiments of the connection means 100 of the invention or of single components thereof, and single features which may be applied in any embodiment in accordance with the invention irrespective of other features where considered to be reasonable by the skilled person, shall be described, in particular by making reference to FIG. 19 or FIG. 19A to FIG. 28, respectively.

In order to facilitate understanding of the described embodiments, reference numerals are indicated, the general description or association of which may predominantly be found in FIGS. 1 to 18.

In another preferred embodiment, the present invention provides a particular lateral mobility and/or pre-centering.

External functional means 400, e.g., disposable cassettes, may comprise a multiplicity of functional means that simultaneously need to be aligned in three dimensions. Frequently, it is intended to align these functional means, e.g., connectors, sensors, actors and the like, by or relative to corresponding functional means and/or arrangements of treatment apparatuses 300.

A basic alignment and/or fixation of the entire external functional means 400 may usually be effected with the aid of a separate means. Typically a centering latching of the external functional means 400 to the chassis 47 of the treatment apparatus 300 and/or a fixation of the external functional means 400 by pressing and/or installation in form closure connection between the chassis 47 of the treatment apparatus 300 is performed. Optionally, a rubber plate 49 and/or a door panel may be used as a cover means 85 (see, e.g., FIG. 3).

When two external functional means 400 are to be taken into fluid communication with each other, the orientation among the connection means 100 and the connector subassembly 200, or among a connection means 100 of a first external functional means 400 and a connector subassembly 200 of a second external functional means 400 may take place directly by means of the inner pipe 1 and of the outer pipe 3 of the connection means 100 and the connection pipe 5 of the connector subassembly 200.

A connection of the connection means 100 and/or of the connector subassembly 200 to a port of a treatment apparatus 300 may, for example, be effected with the aid of thread and/or a bayonet catch and/or via a pivotal yoke (as, e.g., in the case of the rinse port of the current 5008 dialysis machine by the company Fresenius Medical Care, Bad Homburg, Germany).

Hitherto there was the problem, e.g., that deviations of the spacings of the pipes (inner pipe 1, outer pipe 3, connection pipe 5) between the systems or connection systems could generally occur in cases of inaccuracies of the single components and/or during assembly of the single components into subassemblies.

Due to the basic alignment and/or fixation of an entire external functional means 400 relative to an entire treatment apparatus 300 and/or a second external functional means 400 with the aid of a superordinate means, for example a pressing device, a (further) lateral offset of the connection systems could additionally occur in the prior art owing to tolerances or manufacture.

In such a case, fluid connections could only be effected in an optimal manner if both the connection means 100 and the connector subassembly 200 could be taken into the connection positions at a sufficiently low lateral deviation of the respective associated connection axes (e.g., center axes 81, 83).

In a typical conventional arrangement including several connection pipes 5 of external functional means 400, the maximum admissible lateral positional deviation of a connection opening, e.g., of the inner pipe 1, relative to, e.g., the connection opening of the connection pipe 5 e.g., may be about +/−0.2 mm.

Up to such a positional deviation the connection means 100 and the connector subassembly 200, in particular the connection pipe 5 of the connector subassembly 200, might still achieve mutual centering under a sufficiently low lateral force of, for instance, less than 10 N through a flexure in the connection position without causing leakages.

In the reality of one of the multi-connector arrangements mentioned in the foregoing, however, lateral deviations of about up to +/−1.5 mm of the associated connector opening positions after the basic alignment and fixation may occur.

In order to allow successful inward telescoping of the associated pipes (inner pipe 1, connection pipe 5 and outer pipe 3), they preferably require correspondingly configured guiding funnels 87 in combination with an equally high lateral mobility of at least one in a case of two connection partners, i.e., of the connection means 100 and/or the connector subassembly 200 relative to each other.

This lateral mobility may preferably be guaranteed by a pivotal mount 455 of the connection means 100 of the invention relative to the chassis 47 of the treatment apparatus 300.

The represented mounting type advantageously results in a sufficient lateral mobility of the connection opening of the inner pipe 1 of the connection means 100 of the invention relative to the chassis 47 of the treatment apparatus 300.

At a sufficient distance from the connection opening of the inner pipe 1 (preferably about 5 to 20 times the diameter of the connection pipe 5), the outer pipe 3 possesses a spherical shape which is mounted rotatably and/or with little play in corresponding hemispherical sockets, i.e., the upper part 451 and the lower part 453 of the support means 45 (see FIG. 3 and FIGS. 24A-C).

In order to secure lateral mobility it is, of course, also possible to employ other constructional options.

As the connection means 100 of the invention may also be used in a horizontal position under the influence of gravity, and as the lateral mobility means usually is subject to friction and therefore not automatically resetting, a pre-centering means is preferably used in accordance with the invention.

The pre-centering means preferably aligns at least one of the connection means 100 of the invention and/or of the connector subassembly 200 in a tolerance center prior to a renewed connection.

These pre-centering means may preferably ensure that a maximum lateral force among the connection means 100 of the invention and the connector subassembly 200 during the connection is limited to a predetermined value, for example somewhat less than about 10 N.

The pre-centering means is of particular advantage if the connection means 100 of the invention and the connector subassembly 200 might already adopt an excessive laterally deviating position prior to the connection due to their lateral mobility. In such a case a correspondingly larger guiding funnel 87 might then be necessary which would, however, generally be undesirable as the structural size of the arrangement of the connection means 100 of the invention would then increase in an unfavorable manner.

Figure 23A:
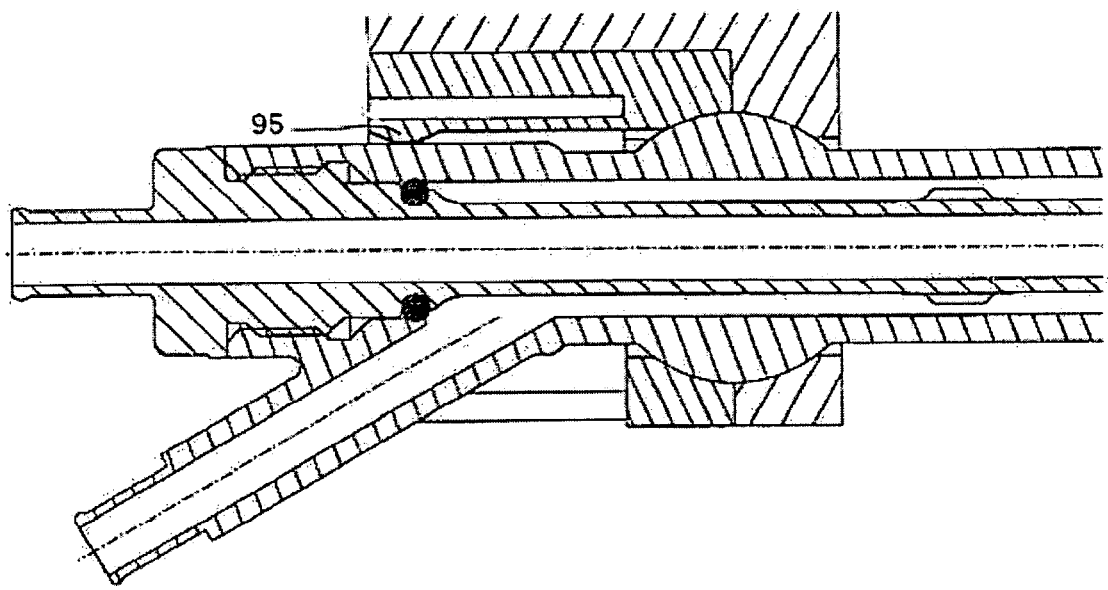
FIG. 23A shows a longitudinal sectional view of a lateral compensation in a design A in a basic position.
Figure 23B:
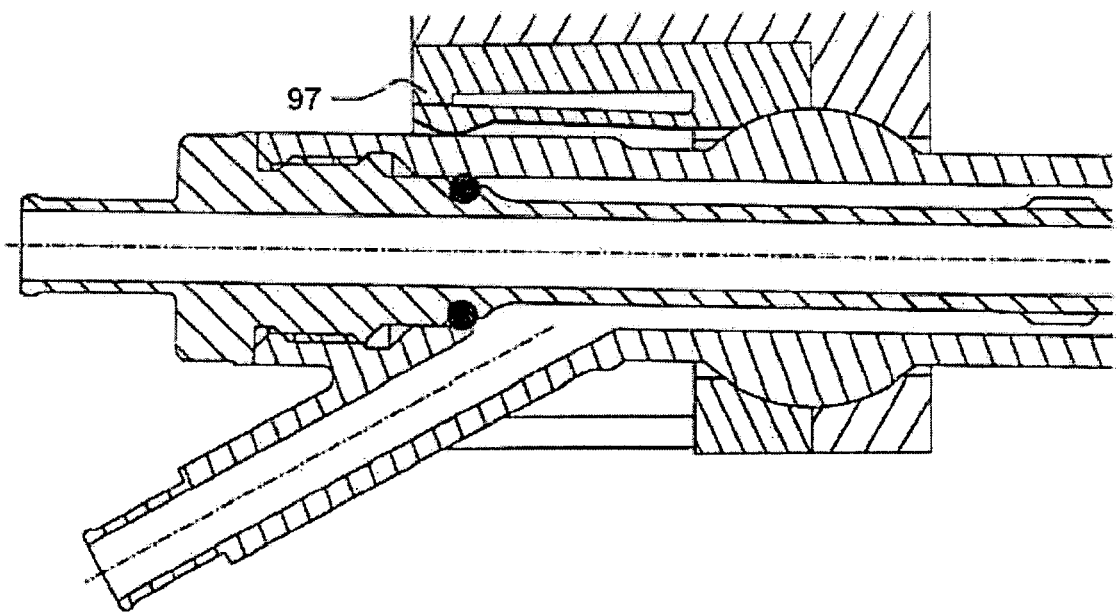
FIG. 23B shows a longitudinal sectional view of the lateral compensation of design A in a deflected position.

FIGS. 23A and 23B show an embodiment of pre-centering through the intermediary of springily deflectable tongues or flexible pre-centering tongues 95 (preferably three tongues).

The flexible pre-centering tongues 95 may bring the connection means 100 into a zero position or basic position, respectively, and at the same time exert a sufficiently low lateral force even in the event of a maximum deflection.

Pre-centering stops 97 may guarantee a limitation of the lateral deflection to the maximum admissible value (in a given case depending on the dimensions of the arrangement of the guiding funnel 87).

Figure 24A:
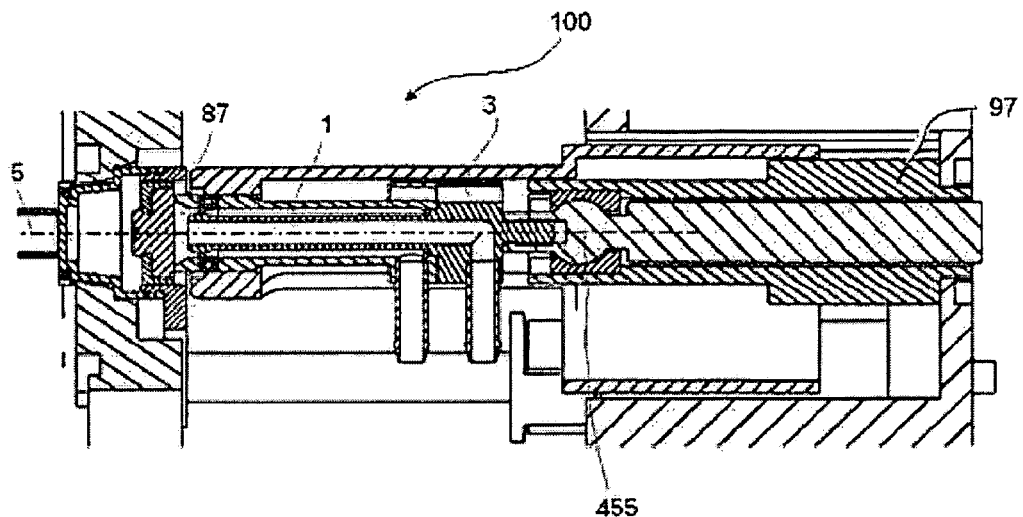
FIG. 24A shows a longitudinal sectional view of a lateral compensation in a design B in a basic position.
Figure 24B:
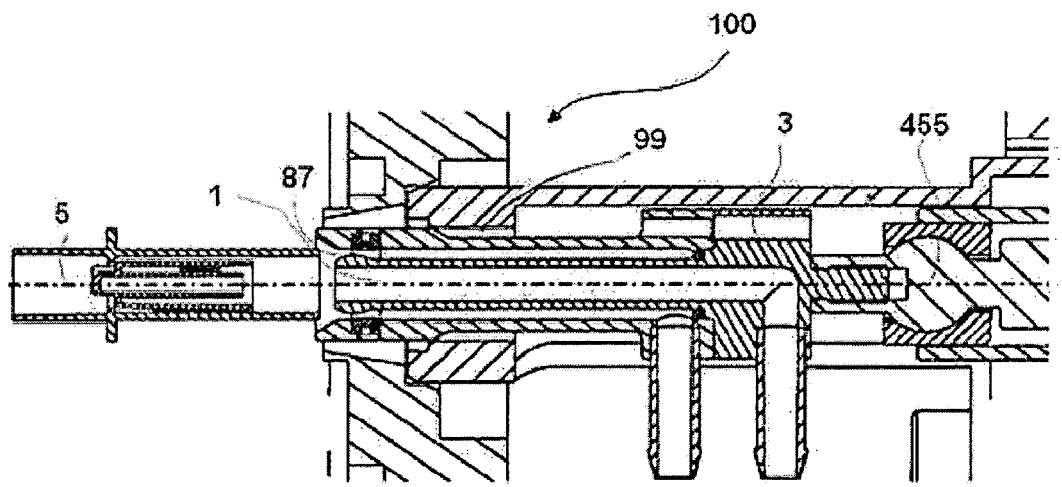
FIG. 24B shows a longitudinal sectional view of the lateral compensation of design B in a pre-centering position.
Figure 24C:
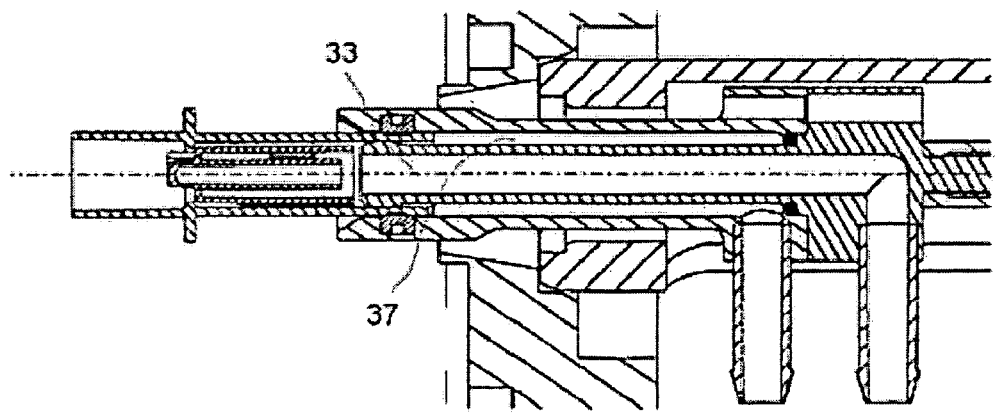
FIG. 24C shows a longitudinal sectional view of the lateral compensation of design B in a connection position.

FIGS. 24A to 24C show an alternative arrangement in which the pivotal mount 455 is realized as balanced scales at an horizontal orientation. From the basic position of FIG. 24A into an intermediate position of FIG. 24B, the outer pipe 3 is guided by a pre-centering tube 99 until an opening of the inner pipe 1 of the connection means 100 of the invention exhibits an overlap with the guiding funnel 87 to the mouth of the connection pipe 5 of the connector subassembly 200.

Starting from this position and to a connection position according to FIG. 24C and beyond, the pre-centering tube 99 gets disengaged, so that no resetting spring forces may act laterally on the connection partners as in previously known arrangements.

In a preferred manner, the fluidic connection conduits of the inner lumen 33 of the inner pipe 1 and of the outer lumen 37 of the inner pipe 1 are realized as easily movable and easily bendable tube conduits, in a particularly preferred manner of silicone rubber.

An arrangement of the fluidic connection conduits as closely as possible near an articulation center point of the pivotal mount 455 is preferred in such a case. In order to reduce the lateral deflecting forces acting on the connection means 100 it may be particularly advantageous to provide the tube conduits or portions thereof with a spiral form.

It may furthermore be particularly advantageous to align and/or immobilize or fix the tube conduits in such a manner that the lateral deflecting forces due to tube connections in the central pre-centering position are approximately zero.

In an extreme deflected position of the pivotal mount 455, preferably all of the lateral forces acting on the connection should be less than the maximum admissible lateral force.

In another preferred embodiment, the present invention provides a lateral, axial and/or angular fine alignment and/or a tolerance compensation.

The relevant operations of tolerance compensation shall in the following be explained with reference to a representation of the movement processes during the connection.

Starting from a basic position of the connection means 100 (e.g., according to FIG. 4 or FIG. 24A) or from a coupling position (e.g. according to FIG. 7) to a position according to FIG. 24B, the pre-centering described in the foregoing is applied.

From this position according to FIG. 24B the connection pipe 5 has penetrated minimally into the guiding funnel 87 of the outer pipe 3, so that the guiding funnel 87 may fulfill the essential tasks of further centering the connection means 100 or the inner pipe 1 and the connector subassembly 200 or the connection pipe 5.

In a further connection movement, starting from the position according to FIG. 8 a contact of the outer contour or of an end face of the touch-prevention panel 31 of the connection pipe 5 with a location on the guiding funnel 87 and thus further lateral centering to the position according to FIG. 9 is obtained, which represents the termination of the funnel centering movement.

The last part of lateral centering may be carried out by the widening 39 of the inner pipe 1 after an initial contact with the rounded jacket surface of the inner wall 7 of the connection pipe 5; see, for example, FIG. 10.

From this position on, fine centering is completed for all further introduction paths of the connection means 100 and of the connector subassembly 200. The preferred globularly spherical shape of the widening 39 in combination with the outer diameter of the inner pipe 1 and in combination with the inner diameter of the connection pipe 5 having a relative larger size by about 5% to 30% may be suited to allow a complete lateral tolerance compensation with the aid of the pivoting movement of the treatment apparatus 300 as described in the foregoing. The maximum angular offset between the connector axes or center axes 81, 83 produced in the process advantageously does not result in a mechanical collision or in a leakage of the main seal and/or of the redundancy seal.

In a preferred embodiment, the tolerance of the axial offset between the connection means 100 of the invention and the connector subassembly 200 is about +/−1.5 mm. This tolerance dimension may lead to reduced complexity of manufacture of the participating structures.

Also with regard to the axial orientation between the two connection systems—in particular in cases of multiple connections operated in an automated manner—clear tolerances may come about in external functional means 400, e.g., in cassette arrangements.

The demands for high compatibility with axial tolerances may even become higher when it is desired that the single components of the connection system of the treatment apparatus 400, including the drive mechanism or drive unit, should as far as possible be adapted for assembly and/or replacement without individual calibration.

Furthermore, it is desirable for the drive mechanisms of the treatment apparatus 400 to have referencing means, path measuring means and/or drive units that are as simple and low-cost as possible.

Thus it may, for example, be sufficient to represent an absolute reference position for the linear drive with the aid of a photoelectric barrier and/or to determine the covered distances solely by counting stepping motor pulses.

In the present case, the elements of the two connection systems may be adapted such that an axial tolerance of about +/−1.5 mm is admissible for any relevant positions of the connector arrangement.

The axial tolerance compatibility in accordance with the invention may partly also derive from the fact that the main seal and/or the redundancy seal are radial seals in interaction with substantially cylindrical connection pipes 5. In detail, FIGS. 12, 14 and 15 illustrate how both a secure connection and a secure open position or closure position of the connector subassembly 200 of an external functional means 400 may be ensured in all of the relevant connection positions.

In another preferred embodiment, the present invention provides an optimized protection for the connector subassembly 200 of an external functional means 400 against touch and/or cough. The optimized protection against touch and/or cough may in particular be advantageous for the fluid-conducting inner region of the connection pipe 5 that is critical in terms of hygiene.

The present invention further allows an improved sterilization capability, in particular an improved gas sterilization capability.

Customarily, previously known usual connectors of external functional means 400 include a closure cap or a stripping film which must be removed manually prior to the beginning of the connection.

Following removal of these protective means, the mouth of the conventional connector or of the conventional connection means is not protected any more against the entry of foreign matters by air-borne transmission, for instance due to coughing or sneezing.

As a countermeasure, the connection pipe 5 of the external functional means 400 has been known to be generally equipped with another external tube structure, compared to which the actual connection pipe 5 is receded so far that a human finger and the end face of the connection pipe 5 may not get in direct contact in the case of inadvertent touch.

A new approach in accordance with the present invention is represented by the touch-prevention panel 31 (in FIGS. 19A and 19B) in the positions according to FIGS. 7 to 12 and 14 and 15.

In accordance with the representation in the figures, the touch-prevention panel 31 is retained on the external functional means 400 by means of a latching arrangement 29 (e.g., FIG. 2) from its assembly until insertion of the external functional means 400 in the treatment apparatus 300.

The touch-prevention panel 31 covers the end face of the connection pipe 5 with segmented and/or bendable segments. As a result, the mouth of the connection pipe 5 may advantageously not be touched and contaminated. Instead, it may advantageously be innocuous to touch the touch-prevention panel 31, for instance with one finger.

Starting from the position shown in FIG. 7 (corresponding to the first contact between the end face of the outer pipe 3 and the associated surface of the touch-prevention panel 31), the touch-prevention panel 31 is propelled by the outer pipe 3 and advanced further. In this case, the bending segments fold in such a way that mechanical contact between outer surfaces of the touch-prevention panel 31 and the surfaces of the connection pipe 5 and/or the surfaces of the inner pipe 1 and/or the funnel surfaces of the outer pipe 3 may advantageously not come about at any point of time.

The touch-prevention panel 31 may be configured in such an angularly tolerant manner that an angle in the axial direction or direction of center line between the connection means 100 and the connector subassembly 200 of not equal to zero may be allowed without impairing the function discussed.

The reception space 23 may be configured to be sufficiently spacious or amply for being able to accommodate the touch-prevention panel 31 in any position of the connection pipe 5 while involving low forces.

Due to its latching and due to friction of the bent segments, a secure retention of the touch-prevention panel 31 may be provided.

In contrast with some conventional touch-prevention caps or touch-prevention stripping films, the touch-prevention panel 31 does advantageously not interfere with the known methods of gas sterilization.

Just like the remaining external functional means 400, the touch-prevention panel 31 may advantageously be manufactured cost-efficiently of thermoplastic materials by injection molding.

After its use, the position of the touch-prevention panel 31 which is now not perceivable or seen on the surface of the external functional means any more, may signal to the user that the external functional means 400 has already been used.

The touch-prevention panel 31 advantageously need not be removed in contrast with a conventional closure cap and may guarantee unfailing touch protection for the connection opening.

It may alternatively also be realized as a cough-protection panel as described in EP 0 966 985 B1, the relevant contents of disclosure are herewith incorporated by way of reference. Thus, a particularly good protection of the connection assembly or of the connection means 100 of the invention, also against coughing or transfer of foreign matter droplets via the air may advantageously be ensured.

The end side of the free end 6 of the connection pipe 5 represents a potential contamination zone. As is shown in FIG. 10, a peripheral internal chamfer 8 or internal rounding is provided at the free end 6 of the connection pipe 5. The internal chamfer 8 preferably does not contact the widening 39. Only the transitional area of the internal chamfer 8 or of the rounding to the smooth pipe portion of the connection pipe 5 contacts the widening 39 of the inner pipe 1, so that germs possibly present in the contamination zone may not be carried over into the connection pipe 5.

This fine centering may advantageously allow or favor a first contact of relevant surfaces of the connection pipe 5 and/or of the inner pipe 1 that is admissible in terms of hygiene.

In this way, an entrainment of contamination into the relevant jacket surfaces of the connection pipe 5 may advantageously be prevented even if a contamination of the end face of the connection pipe 5 or of the funnel surface, or of the guiding funnel 87 of the outer pipe 3 might nevertheless have occurred.

In the case of external functional means 400 for only a single use, a protection against reuse may be desired. Likewise, it may be desired that no more residual liquids may exit from the connection opening of the connection pipe 5 of the connector subassembly 200 following removal of the external functional means 400 from the treatment apparatus 300.

In another preferred embodiment, the present invention therefore provides a protection of the connector subassembly 200 against reuse and/or trickling out. In addition, an improved gas sterilization capability may in turn advantageously be ensured.

In the solution in accordance with the invention it is not only possible to indicate a first use of the external functional means 400 having taken place, but an inadmissible second use may also be prevented.

It is another advantage of the solution in accordance with the invention, for instance when it was forgotten to remove a tamper protection, that the external functional means 400 and/or the treatment apparatus 300 is not being damaged later on—in particular in cases of automatic connection systems.

In another preferred embodiment, the present invention provides a protection of the connector subassembly 200 against reuse and/or trickling out. In addition, an improved gas sterilization capability may in turn advantageously be ensured.

In accordance with the invention this is achieved through the closure sleeves 9, for example according to FIGS. 21A, 21B, 22A, 22B as well as 26.

Figure 22A:
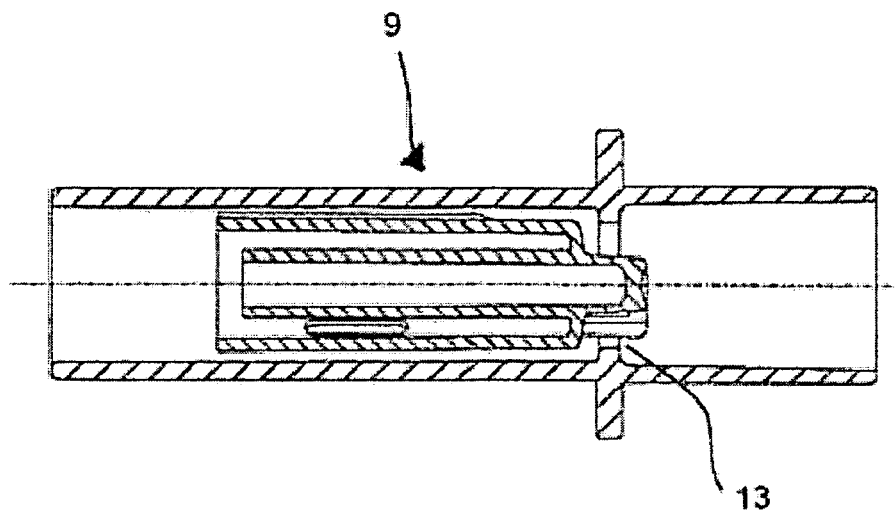
FIG. 22A shows a longitudinal sectional view of the closure sleeve of design B in a basic position.
Figure 22B:
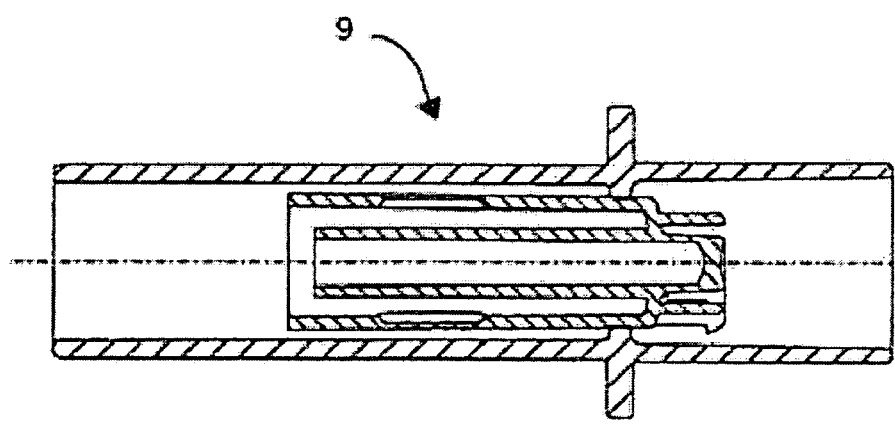
FIG. 22B shows a longitudinal sectional view of the closure sleeve of design B in a closure position.

In FIGS. 22A and 22B a closure sleeve 9 with an integrated drip-protection element is shown. The drip-protection element is obtained by providing several pipe portions in a concentrically nested configuration, thereby creating narrow ring gaps which "suck in" drops by capillary effect and thus prevent them from trickling out. A closure sleeve 9 having such a construction may be used in a multiplicity of quite different external functional means (disposables), whenever the trickling out of liquid may occur following disconnection. In particular a use in the dialysate ports of dialyzers is conceivable.

Figure 26:
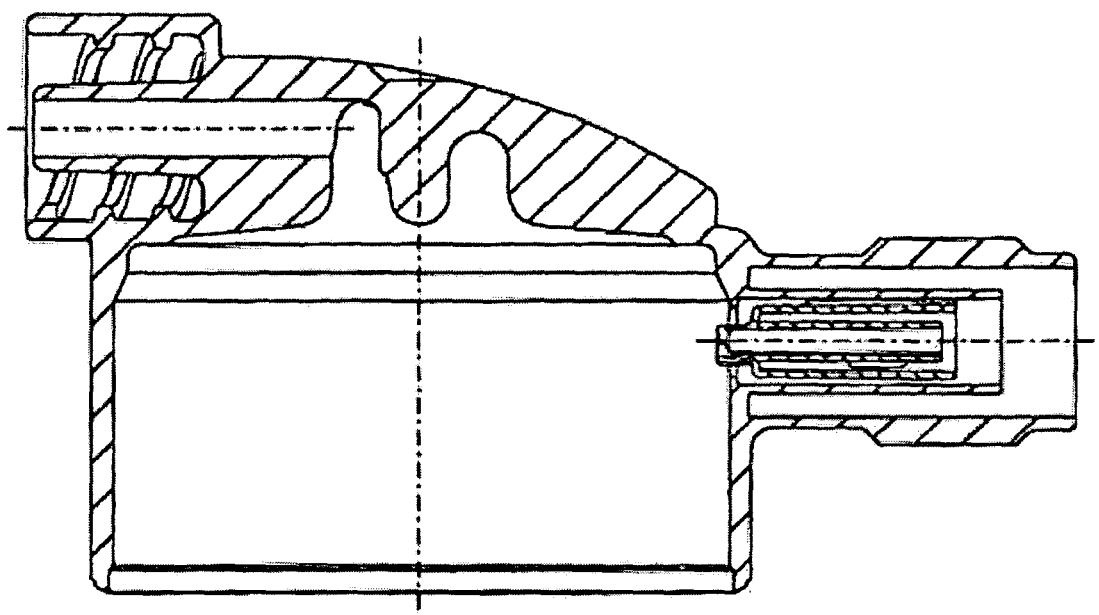
FIG. 26 shows a longitudinal sectional view of a dialysis filter including a connector subassembly inside the dialysate port.

FIG. 26 shows an end cap of a dialyzer with inserted closure sleeve 9. It is conceivable to use the closure sleeve 9 shown in FIGS. 22A and 22B as a retrofitting kit for dialyzers that are already commercially available. The closure sleeve 9 having an integrated drip-protection element is initially opened so that gas sterilization and/or vapor sterilization may be performed. It is closed irreversibly after the end of the single use of the external functional means, with the drip-protection element preventing liquid drops from trickling out from the connection piece.

FIG. 22A shows the flow passage position; FIG. 22B shows the closure position.

In the framework of the manufacture of the external functional means 400 the closure sleeve 9 may be made of the same low-cost thermoplastic materials as the remaining constituent parts of the external functional means 400. It may be retained by the latching arrangement 13.

The initial arrangement may advantageously allow any form of gas sterilization in a particularly simple and effective manner.

Due to the stress-free latching, damages to the external functional means 400 do not occur during sterilization—in particular also during vapor sterilizations.

After termination of the fluid treatment, the connection means 100 of the treatment apparatus 300 of the two connection systems (connection means 100 and connector subassembly 200 or external functional means 400 or treatment apparatus 300) may be telescoped further in, whereby the closure sleeve 9 arrives in the closure position.

This may advantageously result in a liquid-tight and/or non-releasable expansion-type seal of the connection pipe 5 of the external functional means 400 between the associated topologies of closure neck 17 with closure collar 11.

A reuse may hereby advantageously be precluded and may also be recognized securely in the framework of the initial test following installation of the external functional means 400 (e.g., pressure keeping test).

The treatment apparatus 300 and/or the external functional means 400 are advantageously not damaged upon attempted reuse.

When the connection means 100 and the connector subassembly 200 are disconnected, a residual space including a residual liquid that possibly should not leak to the environment still remains in the connection pipe 5.

Due to the narrow arrangement of coaxial pipe structures and/or through bores in combination with the small distance of the end face of the inner pipe 1 from the contacting end face of the closure sleeve 9, only a little volume of residual liquid may advantageously remain, which may moreover advanta-geously be prevented from dripping off through the narrow structures due to the capillary effect.

This capillary design may be integrated directly in the connection pipe 5 in the case of the known rinsing connector or on-line connector.

A closure sleeve may be omitted altogether in this application. The number of constituent parts of the connector is reduced to only two parts while guaranteeing the gas sterilization capability in contrast with conventional means.

Another advantageous application of the protection against reuse and of the protection against trickling out may result from the dialysate ports of the dialysis filter in accordance with FIG. 26.

Previously, closure caps usually had to be shipped jointly and installed manually after use in order to achieve a protection against trickling out of residual dialyzing liquid after use.

The use of the closure caps is particularly inconvenient because they need to be disposed of in accordance with regulations following their removal, and where necessary have to be replaced with new, sterile caps.

Furthermore, it is usually at first necessary to perform an awkward operation of removing an upper machine-side dialysate port, manually install the upper closure cap, then reverse the filter by 180 degrees and perform the same procedure on the other dialysate port for the purpose of preventing the dialyzer from running empty.

The realization of the inner pipe 1 in accordance with the invention and the latched inserted closure sleeve 9 (see, e.g., FIG. 26) may advantageously result in a dialysis filter which may be fully compatible with the customary dialysis filters with regard to the Hansen connector geometry and/or with regard to the connections in connection with filter manufacture. A utilization in any dialysis filter on the market is conceivable.

Possible additional costs during manufacture may in particular be insignificant.

The treatment of the dialysis filter by liquid, gas and/or vapor during manufacture is advantageously furthermore possible without any restrictions. A mixed use of filters with and without closure sleeve 9 may equally be ensured through corresponding realization of the connection means 100 relative to the Hansen connector geometry.

The present invention thus provides an optimized protection against reuse and/or a protection against trickling out with optimized handling.

The one of the two drive mechanisms is the linear drive for the main connecting movement which admits not only two positions but at least the three positions of basic position, connection position and closure position, and also provides further positions with a corresponding connection technique as described in the foregoing.

Preferably, electrical drive mechanisms in combination with absolute path measurement systems and free programmability of the displacement programs are utilized.

The use of a threaded spindle/threaded nut for converting the rotational movement into a linear movement is particularly cost-efficient in comparison with other converting options. Its use may moreover present the advantage of holding the linear drive in the respective current position in the event of malfunction if a sufficiently low thread pitch is selected.

The second drive complex relates to the drive mechanism of the movements necessary for placing and removing the closure cap or rinsing cap 41. Here, a combined pivotal and/or lifting drive which is electromotorically driven may preferably and advantageously be utilized. Other types of movement and actuation, such as an oblique slide movement or a drive by means of pneumatic cylinders, are equally encompassed by the invention.

Finally, it may advantageously be possible to also mechanically derive the movements of the rinsing cap pivotal drive mechanism 43 from the stroke movement of the linear main drive through corresponding stops or control cams. This technique was also successfully put into practice in experimentation.

FIG. 4 shows a radial seal which may advantageously do away completely with elastomer sealing rings (having inherent dead-space problems). At least one of the two sealing mates (the sealing body 59 of the outer pipe 3 or the fluid insert 411 of the rinsing cap 41) is preferably manufactured in one piece of a material that is suitable for sealing as well as for configuring the rinsing space such as, for example, PTFE.

The elastic resilience necessary for sealing may be ensured through a resilient implementation of the sealing zone and/or through an additional reset spring support, for example through an elastomer ring acting in the direction of sealing and/or through correspondingly acting spring constructions (known from the field of rotary shaft seals).

Figure 20A:
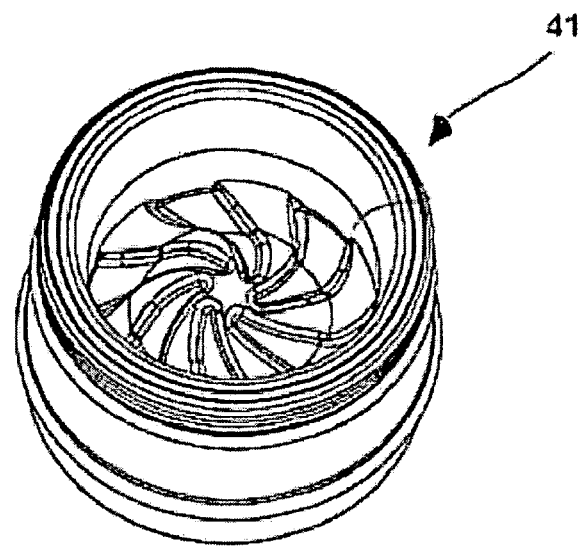
FIG. 20A shows a rinsing cap having a spiral structure in a perspective view.
Figure 20B:
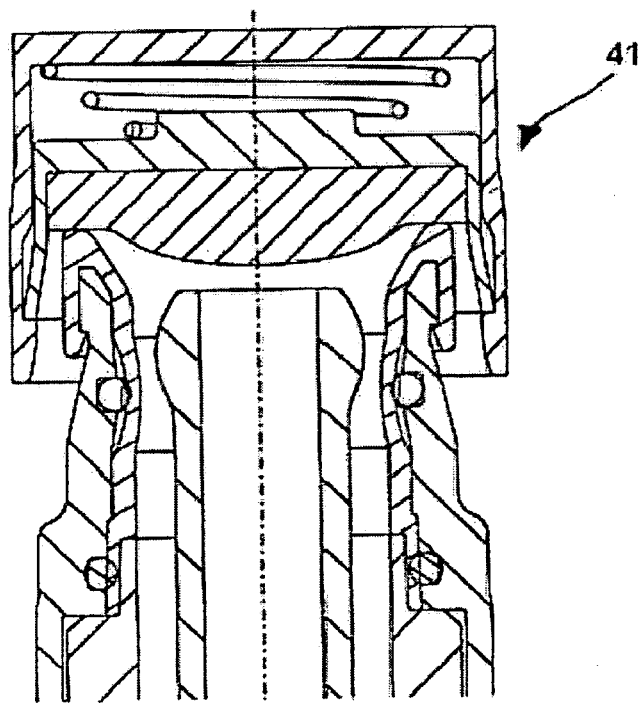
FIG. 20B shows a rinsing cap in an axially sealing design in a longitudinal sectional view.
Figure 21A:
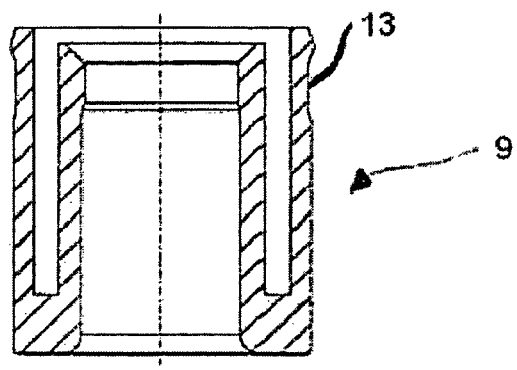
FIG. 21A shows a closure sleeve in a design A in a longitudinal sectional view.
Figure 21B:
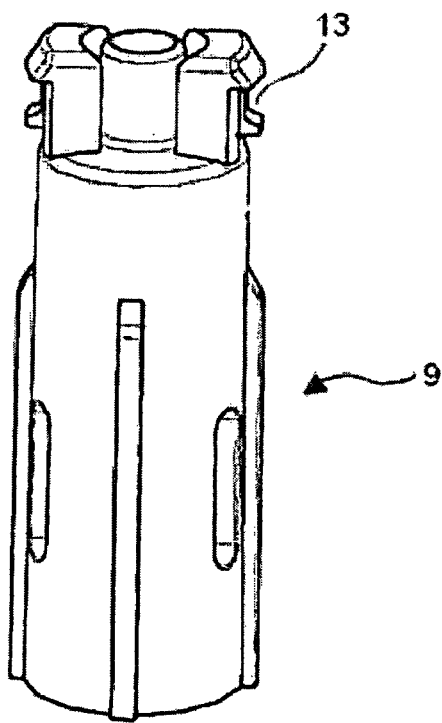
FIG. 21B shows a closure sleeve in a design B with improved drip-protection in a perspective view.

Another variant of sealing the rinsing cap or closure cap against the outer pipe 3 is the axially sealing design shown in FIG. 20B: this involves a fluid insert 411 of elastomer or of PTFE which is placed in an axially sealing manner on the end face of the outer pipe 3. Here, too, there preferably are substantially no more of the typical dead spaces mentioned before. As another advantage there may additionally be particularly good endurance against wear because such an axial seal may automatically adapt axially and angularly to the sealing mate.

Another advantage of this technique may consist in the fact that the partially emptied inner space of the connection means 100 in the region of the widening 39 of the inner pipe 1 substantially does not have a coherent ring of liquid any more when the closure cap or the rinsing cap 41 is removed, and that also the space in front of the end face of the inner pipe 1 is partially emptied from liquids.

The mounting body 413 of the rinsing cap 41 in FIG. 4 is connected to the rinsing cap pivotal drive mechanism 43 by a thread, latch-insertion or bayonet catch. Moreover, the seal of the mounting body 413 against the chassis 47 of the treatment apparatus 300 or the rubber plate 49 is preferably effected in a radially sealing manner. On the end face facing the user, the mounting body 413 furthermore comprises at least one means for transmitting the forces and movements required for disassembling. In a preferred manner this is a groove for disassembling the mounting body 413 which is advantageously adapted for easy and simple operation such as, for example, by means of a coin.

The user may now advantageously take out the rinsing cap 41 without further dismantling of the mechanism and subject both the rinsing cap 41 and the end space of the connection means 100 to a revision, for example. After removing the rinsing cap 41, the surroundings of the head body 57 of the outer pipe 3 are accessible. At the head body 57 of the outer pipe 3 there are several recesses or depressions present on the outside on which a ring wrench tool may attack.

Thus not only revisions but also replacing the rinsing cap 41 as well as the sealing body 59 of the outer pipe 3 (both of which are wear parts) may advantageously be performed by the operating personnel of the treatment apparatus 300 without any particular complexity.

The connection means 100 of the invention according to FIGS. 3 and 4 advantageously includes a complete protection against touch and/or cough of all the regions that are relevant in terms of hygiene. In the basic position of the connection means 100, the rinsing cap 41 is mounted in a liquid-tight manner against the chassis 47 of the treatment apparatus 300 or against the rubber plate 49.

The first operation of refitting the treatment apparatus 300 with the external functional means 400 may include fixation of the external functional means 400 in front of the rinsing cap 41 in the basic position. Thus, any contact with the regions that are relevant in terms of hygiene may advantageously be precluded. In the further process, the rinsing cap 41 is drawn off behind the tight cover through the external functional means 400 from the connection means 100 while being inaccessible for touch and for drops of liquid from the surroundings, and pivoted into a further inaccessible space behind the front of the treatment apparatus 300.

For any further operations during use of the fluid connection system including the return of the rinsing cap 41 into the basic position (stand-by position or position for the disinfecting and rinsing operations), the external functional means 400 preferably remains in this covering position.

Figure 25A:
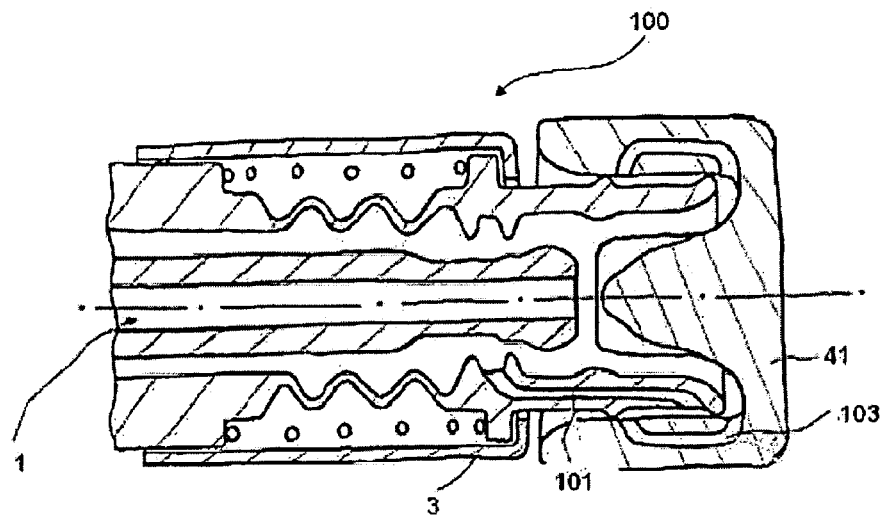
FIG. 25A shows a longitudinal sectional view of an embodiment of the connection means of the invention during a disinfection, a rinsing operation and/or in operation-readiness.
Figure 25B:
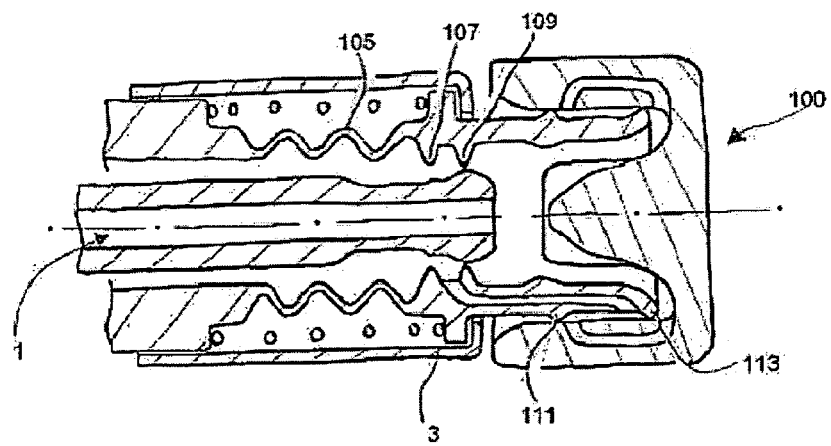
FIG. 25B shows a longitudinal sectional view of an embodiment of the connection means of the invention during an emptying operation and/or at the beginning of a connecting operation.
Figure 25C:
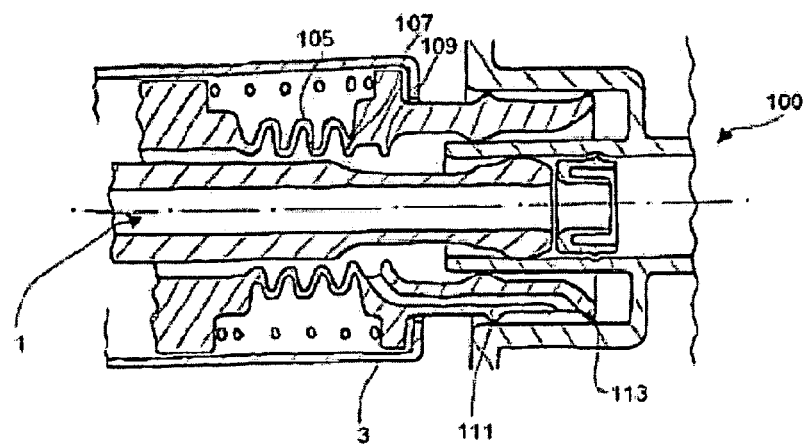
FIG. 25C shows a longitudinal sectional view of an embodiment of the connection means of the invention during the connection and/or a closing operation.

FIGS. 25A to 25C show a particularly optimized design and type of movement of the connection means of the invention 100. Particularly in a horizontal connection assembly, this arrangement may achieve further raised demands with regard to low losses of residual liquid and/or with regard to securing freedom from germs.

FIG. 20A shows a fluid insert 411 of the rinsing cap 41 having a particularly optimized configuration of flow space. Due to a substantially conical contour conformation in combination with spiral-shaped redirecting grooves, the flow exiting from the inner pipe 1 during disinfection and/or rinsing is redirected, preferably with low losses, to the lateral sealing regions between outer pipe 3 and rinsing cap 41 and thereby shifted to a rotational flow.

In a global view, the flow space through the optimized conformation was configured to be particularly narrow in order to be able to ensure overall high flow velocities and good fluid exchange.

FIGS. 25A-C show the components of inner pipe 1, outer pipe 3, and rinsing cap 41 for the further optimized design. The outer pipe 3 is now configured to be axially movable relative to the inner pipe 1.

In order to avoid radially sealing shifting sealing arrangements inherently involving problems of wear and/or dead spaces, this shifting capability is preferably realized with the aid of the shown bellows arrangement 105 of a plastics material such as PTFE.

In a geodetically lowest location of the outer pipe 3, a passage 101 is arranged which merges in the direction of return flow between two inner ring beads 107 and 109 which are capable of forming a switchable flow throttle due to the shifting capability of the inner pipe 1 relative to the outer pipe 3 in combination with corresponding diameter ratios relative to the sealing head or sealing body 59.

At least one further passage 103 is located, in a preferred manner also in a lowest location, in the rinsing cap 41. In the case of the connection comprising the rinsing cap 41, the outer pipe 3 comprises two external ring beads 111 and 113.

FIG. 25A shows the locations of these components during disinfection, rinsing and operation readiness. The rinsing cap 41 is inserted in the outer pipe 3 to a maximum depth. The external ring bead 111 serves as a final seal against the environment. The further external ring bead 113 serves as a stripping means for possible encrustations in the region of the ring bead 111 while forming a flow redirection in this location for disinfection and rinsing.

In this position the inner pipe 1 is retracted to such a degree that the outer diameter of the sealing body or of the sealing head forms a flow throttle against the further inner ring bead 109.

For the major part a flow takes place through the rinsing cap 41, through the passage 103 in the rinsing cap 41 into the annular region between the external ring beads 111, 113, into the passage 101 in the outer pipe 3, and from there into the outflow space behind the sealing body or sealing head. The mouth-side region of the outer pipe 3 is advantageously subjected to particularly intense rinsing action, wherein the further external ring bead 113 is cleaned from two sides, while the external ring bead 111 is rinsed on its side towards the annular region.

A smaller part of the rinsing fluids makes its way through the throttling location at the sealing head. During operation readiness until the next removal of the rinsing cap 41, the outer pipe 3 advantageously remains disinfected, well-rinsed and/or free from possible deposits in a particularly large region extending as far as the external ring bead 111.

FIG. 25B shows the positions of the components during the processes of emptying and at the beginning of the subsequent connecting operations to the connection pipe 5 of the connector subassembly 200.

After completion of the disinfection and/or rinsing processes, the inner pipe 1 moves a further distance away from the end face of the outer pipe 3. This results in approximate sealing between the further inner ring bead 109 and the outer diameter of the sealing head.

The lumen of the outer pipe 3 is now coupled to the waste water network of the treatment apparatus 300, either directly or via a conveying means. The inner pipe 1 is connected, either directly or via a conveying means, to a gas port. The liquid is discharged towards the waste water network by generating a pressure difference or by activating a conveying means.

In the represented passage regions in the area of the tip of the inner pipe 1 and of the outer pipe 3 and of the rinsing cap 41 which is adapted particularly for this purpose (in short: mouth region) there only remains a particularly small volume of liquid which needs to be removed for drying the connection-relevant connector regions. Due to the narrow flow spaces, this volume of liquid may be relocated in a particularly effective manner into the bellows region or bellows arrangement 101 of the annular lumen having a geodetically lower position, from where it can not return into the mouth region in a horizontal connection assembly.

The relevant spaces in the mouth region of the connection means 100 and of the rinsing cap 41 are freed from liquid to such a complete degree or extent that only a small film of residual liquid remains on the surfaces, which can not result in a leakage of residual liquid to the environment any more when the rinsing cap 41 is drawn off later on.

This effect is also supported by the fact that the surfaces impinged by flow are preferably provided with a hydrophilic coating. In this way, only strongly adhering liquid films but no easily movable, large drops of liquids may form on the surfaces.

When the rinsing cap 41 is subsequently drawn off, the inner pipe 1 is particularly far away or far removed from the end face of the outer pipe 3 and from the rinsing cap 41. In addition, the entire mouth region that is of relevance during the following processes is freed virtually completely of liquid or movable residual liquid.

As a result, the inner pipe 1, which is far receded and which is particularly relevant for the subsequent sterile connection from the point of time immediately prior to withdrawal of the rinsing cap 41 until completion of the following connecting operations, is provided with a particularly effective protection both against touch and against possible contaminations with non-sterile or soiling substances, in particular drops of liquid, which may during the subsequent rinsing cap and connection movements enter the mouth region of the internal connector subassembly 200 which is then open against the non-sterile environment.

At the beginning of connection to the connector subassembly 200, the inner pipe is particularly far removed from the non-sterile environment of the treatment apparatus 300.

FIG. 25C shows the optimized design in the position of completed connection until the final change of position into the closure position of the closure sleeve 9. During the connection, the inner pipe 1 is increasingly displaced in a forward direction towards the end face of the outer pipe 3. At the same time, both external ring beads 111 and 113 seal against the cylindrical wall of the reception space 23. In this way, the functionalities of the outer lumen 37 in combination with the redundant seal and/or in combination with the examination of tightness are maintained. Upon reaching the connection position and upon change to the closure position, the inner pipe 1 may increasingly be displaced towards the end face of the outer pipe 3 and thus further on than in a rigid arrangement of the inner pipe 1 relative to the outer pipe 3. In this way, a sufficiently large axial tolerance may be realized at a smaller structural length of the connection pipe 5 and of the reception space 23. Each ring bead may preferably be produced as an inserted sealing ring of elastomer material coated with PTFE.

Figure 27:
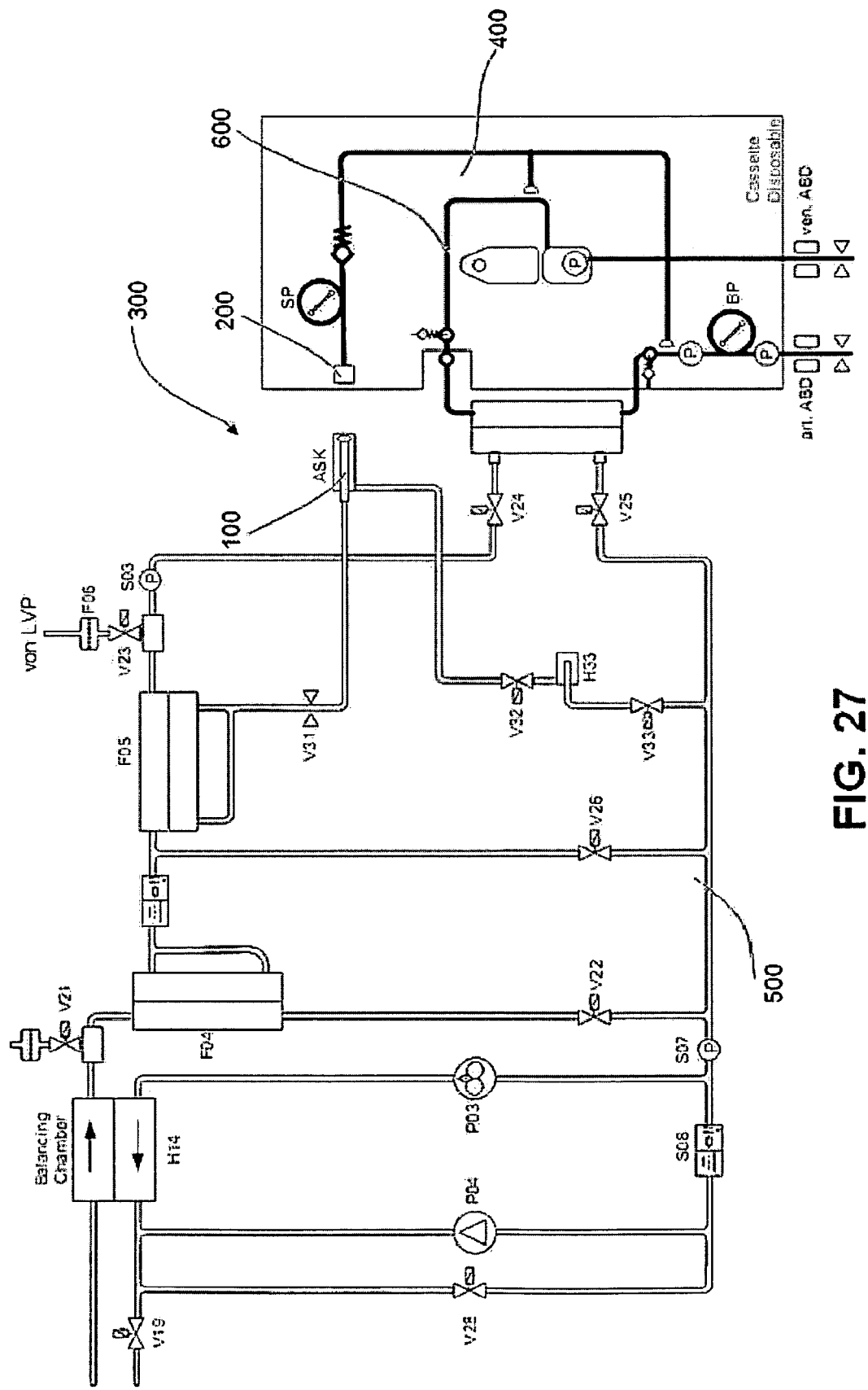
FIG. 27 shows a flow diagram of a treatment apparatus of the invention comprising a connection means of the invention and an external functional means.

FIG. 27 schematically shows the position of the connection means 100 of the invention in a process flow chart of a dialysis machine as a treatment apparatus 300 including dialysate circuit 500 and extracorporeal blood circuit 600. The extracorporeal blood circuit 600 comprises an external functional means 400 which is exemplarily shown as a blood treatment cassette. Such a blood treatment cassette is described, for example, in the German Patent Application No. 10 2009 018 664.6 (representative's file FM19A27) and German Patent Application No. 10 2009 024 468.9. (09/33-d01 DE; FM19B27) filed by the applicant of the present application with the German Patent and Trademark Office on Apr. 23, 2009 and on Jun. 10, 2009, respectively, each having the title "Externe Funktionseinrichtung, Blutbehandlungsvorrichtung zum Aufnehmen einer erfindungsgemäβen externen Funktionseinrichtung, sowie Verfahren" [External functional means, blood treatment apparatus for receiving an external functional means in accordance with the invention, and method], the respective disclosures of which are herewith fully incorporated by way of reference.

The external functional means 400 comprises the connector subassembly 200 as an integral constituent part. The connection means 100 and the connector subassembly 200 form the substitute connection from the dialysis machine to the blood treatment cassette. In FIG. 27, the connection means 100 and the connector subassembly 200 are represented in the non-connected state.

Figure 28:
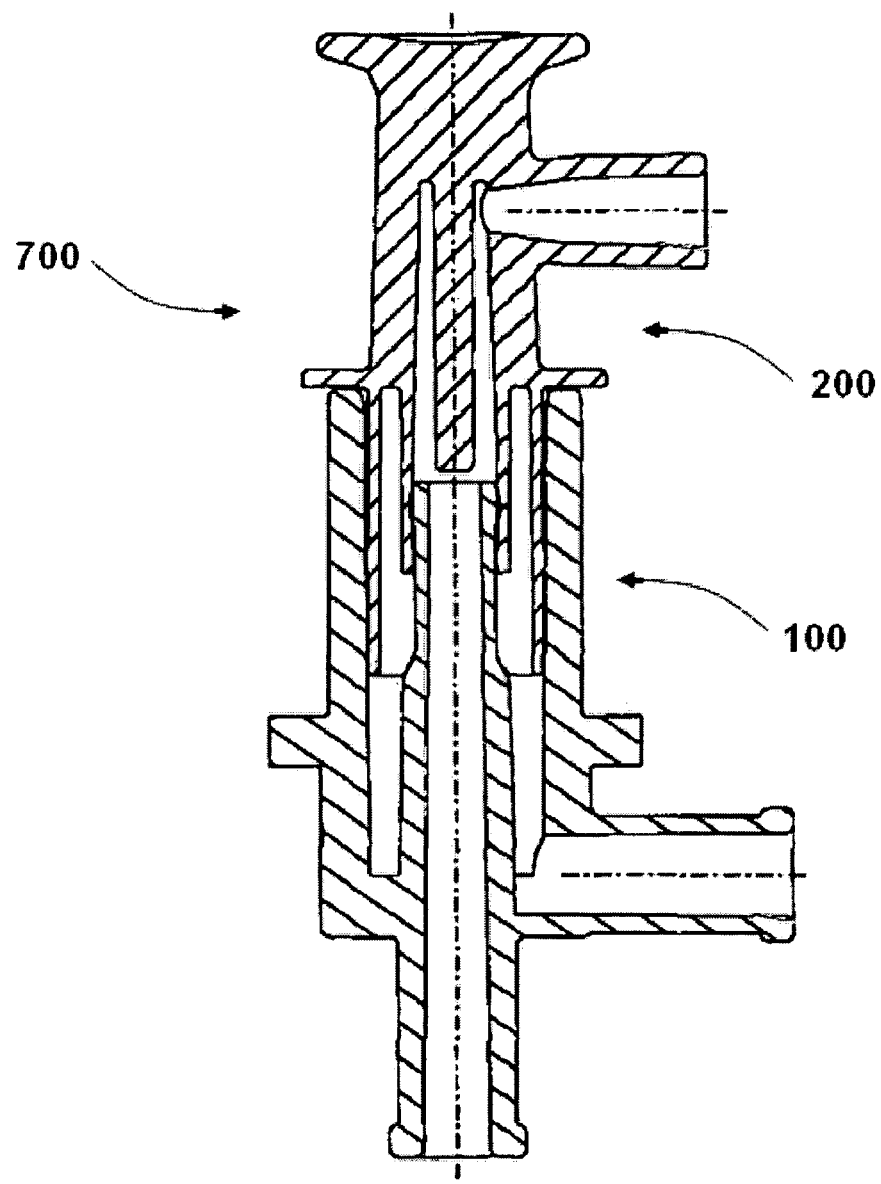
FIG. 28 shows a rinse port in a longitudinal sectional view.

FIG. 28 shows a rinse port 700 in a longitudinal sectional view.

The rinse port 700 comprises a realization of both connector subassemblies or connection half-assemblies, i.e., both the connector subassembly 200 and also the connection means 100. Such an arrangement is particularly used for applications in which a connection is achieved manually and/or pre-centering is achieved directly through the intermediary of the connector subassemblies and/or additional means for lateral tolerance compensation are omitted and/or the internal connector subassembly as well as the external connector subassembly are equally realized as disposables and/or a closure sleeve may be omitted because the capillary drip-protection element is already integrated integrally or by material connection, respectively, in the connection pipe of the external connector subassembly while a closure sleeve as drip-protection element is not required due to the low pressures in this location at which possible residual liquids are banked up at the external connector subassembly.

FIG. 28 furthermore illustrates that both connector subassemblies, each taken for itself, are provided with an effective classical touch protection through the intermediary of retracted connection-relevant inner connectors (inner pipe and connection pipe).

LIST OF REFERENCE NUMERALS

| Reference Numeral | Description |
| --- | --- |
| 100 | connection means |
| 200 | connector subassembly of external functional means |
| 201 | surface of treatment apparatus |
| 300 | treatment apparatus |
| 400 | external functional means |
| 500 | dialysate circuit |
| 600 | extracorporeal blood circuit |
| 700 | rinse port |
| 1 | inner pipe |
| 3 | outer pipe |
| 5 | connection pipe |
| 6 | free end of the connection pipe |
| 7 | inner lumen of the connection pipe |
| 8 | internal chamfer |
| 9 | closure sleeve |
| 11 | closure collar |
| 13 | latching arrangement of the closure sleeve |
| 15 | inner wall of the outer pipe |
| 17 | closure neck |
| 19 | support dome |
| 21 | passage |
| 23 | reception space |
| 25 | support ring |
| 27 | outer wall of the connector subassembly |
| 28 | residual gap |
| 29 | latching arrangement touch-prevention panel |
| 31 | touch-prevention panel |
| 33 | inner lumen of inner pipe |
| 35 | outer wall of inner pipe |
| 37 | outer lumen of inner pipe |
| 39 | widening of inner pipe |
| 41 | rinsing cap |
| 411 | fluid insert |
| 413 | mounting body |
| 43 | rinsing cap pivotal drive mechanism |
| 45 | support means |
| 451 | upper part |
| 453 | lower part |
| 455 | pivotal mount |
| 47 | chassis of a treatment apparatus |
| 49 | rubber plate |
| 51 | fluid port inner pipe |
| 53 | fluid port outer pipe |
| 55 | base body of outer pipe |
| 57 | head body of outer pipe |
| 59 | sealing body of outer pipe |
| 60 | seal |
| 61 | gap |
| 621 | seal |
| 623 | seal |
| 63 | DC motor for pivoting the rinsing cap |
| 65 | DC motor for displacing the connection means |
| 67 | dripping water drain |
| 69 | film potentiometer |
| 71 | Hall sensor |
| 73 | inlet |
| 75 | pivoting lever |
| 77 | magnet on pivoting lever |

-continued

| Reference Numeral | Description |
| --- | --- |
| 79 | return line |
| 81 | center axis of connection pipe |
| 83 | center axis of inner pipe |
| 85 | cover means |
| 87 | guiding funnel |
| 89 | lateral tolerance of connection pipe |
| 91 | redundancy sealing bead |
| 93 | housing front part |
| 95 | flexible pre-centering tongues |
| 97 | pre-centering stop |
| 99 | pre-centering tube |
| 101 | passage in outer pipe |
| 103 | passage in rinsing cap |
| 101 | bellows arrangement |
| 107 | inner ring bead |
| 109 | further inner ring bead |
| 111 | outer ring bead |
| 113 | further outer ring bead |

I claim:

1. A connection means for the fluid connection of at least one first fluid-conducting medical-technical system to one second fluid-conducting medical-technical system, comprising:
at least one first pipe section of the first system;
at least one second pipe section of the second system; and
a pivotal mount for aligning the first pipe section and/or the second pipe section relative to each other,
wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section;
wherein the first pipe section comprises at least one inner pipe, at least one outer pipe, and a space between the inner pipe and the outer pipe;
wherein the second pipe section is a connection pipe; and
wherein the space between the inner pipe and the outer pipe is adapted for receiving at least a portion of the connection pipe.

2. The connection means according to claim 1, wherein the first pipe section is an inner pipe and the second pipe section is a connection pipe.

3. The connection means according to claim 1, wherein the first system and/or the second system is an external, medical-technical functional means.

4. The connection means according to claim 1, wherein the first system and/or the second system is a blood treatment apparatus or a medical analytic apparatus.

5. The connection means according to claim 1, further comprising:
a closure means for short-circuiting or connecting an inner lumen of the at least one inner pipe with the space between the at least one inner pipe and the at least one outer pipe in fluid communication.

6. The connection means according to claim 1, wherein the widening is present on the inner pipe or on the connection pipe.

7. The connection means according to claim 1, wherein the widening is configured to effect a fluidic seal between the first pipe section and the second pipe section when the connection means is in a ready-to-use, connected condition.

8. The connection means according to claim 1, wherein the widening has its largest cross-sectional diameter or its largest circumference in a cross-section in a plane perpendicular to the direction of connection of the first pipe section to the second pipe section, in a region of the widening that is central in the direction of connection.

9. The connection means according to claim 1, wherein the widening has its largest cross-sectional diameter or its largest circumference in a cross-section in a plane perpendicular to a direction of extension of an inner lumen of the pipe section on which the widening is present, in a region of the widening that is central in the direction of connection.

10. The connection means according to claim 1, wherein the widening has a same diameter and/or circumference in at least three different sectional planes through a central point of the widening or in at least three different sectional planes containing a common straight line.

11. The connection means according to claim 1, wherein the diameter or the cross-sectional diameter of the widening is circular.

12. The connection means according to claim 1, wherein the widening is configured such that it may be moved, in the process of connecting the first pipe section to the second pipe section, along a displacement path in the pipe section into which it is being introduced, while maintaining the sealing condition brought about by it; and/or
the widening is configured such that it may be tilted, in the process of connecting the first pipe section to the second pipe section or following completion of connecting, by an angle relative to the direction of flow, while maintaining the sealing condition brought about by it.

13. The connection means according to claim 1, further comprising an additional sealing means.

14. The connection means according to claim 13, wherein the additional sealing means is arranged adjacent to the widening during use of the connection means.

15. The connection means according to claim 1, further comprising a pressure limiting valve.

16. The connection means according to claim 1, further comprising a waste water branch.

17. The connection means according to claim 1, further comprising a pre-centering means for horizontal and/or lateral alignment of the first pipe section and/or of the second pipe section.

18. The connection means according to claim 1, further comprising a touch-prevention panel for preventing an interior from being contaminated and/or the at least one second pipe section from being touched.

19. The connection means according to claim 18, further comprising an external, medical-technical functional means, wherein the touch-prevention panel is retained in the external, medical-technical functional means by a latching arrangement.

20. The connection means according to claim 1, further comprising a means that is mechanically altered and/or moved in the process of connecting such that the completed connection continues to be apparent on the means following disconnection.

21. The connection means according to claim 1, wherein the widening is for connecting the inner pipe to the connection pipe by jamming and/or expanding the inner pipe.

22. The connection means according to claim 1, wherein the widening has the at least one of the spherical, globular, curved, arc-shaped and convex outer surface in a region of the maximum cross-section or diameter, in a direction of flow.

23. A connection means for the fluid connection of at least one first fluid-conducting medical-technical system to one second fluid-conducting medical-technical system, comprising:
at least one first pipe section of the first system;
at least one second pipe section of the second system;
a pivotal mount for aligning the first pipe section and/or the second pipe section relative to each other; and
a pre-centering means for horizontal and/or lateral alignment of the first pipe section and/or of the second pipe section,
wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section;
wherein the pre-centering means comprises at least two springily deflectable tongues.

24. A connection means for the fluid connection of at least one first fluid-conducting medical-technical system to one second fluid-conducting medical-technical system, comprising:
at least one first pipe section of the first system;
at least one second pipe section of the second system;
a pivotal mount for aligning the first pipe section and/or the second pipe section relative to each other; and
a touch-prevention panel for preventing an interior from being contaminated and/or the at least one second pipe section from being touched,
wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section;
wherein the touch-prevention panel comprises a plurality of bendable segments.

25. A connection means for the fluid connection of at least one first fluid-conducting medical-technical system to one second fluid-conducting medical-technical system, comprising:
at least one first pipe section of the first system;
at least one second pipe section of the second system;
a pivotal mount for aligning the first pipe section and/or the second pipe section relative to each other; and
a bellows arrangement,
wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section;
wherein the first pipe section comprises:
at least one inner pipe;
at least one outer pipe; and
a space between the inner pipe and the outer pipe,
wherein the second pipe section is a connection pipe, and
wherein the space between the inner pipe and the outer pipe is adapted for receiving at least a portion of the connection pipe.

26. The connection means according to claim 25, wherein the bellows arrangement is part of the outer pipe.

27. The connection means according to claim 26, wherein the outer pipe further comprises at least one spring member for tightening the bellows arrangement.

28. A connection means for the fluid connection of at least one first fluid-conducting medical-technical system to one second fluid-conducting medical-technical system, comprising:
- at least one first pipe section of the first system; and
- at least one second pipe section of the second system,
- wherein the first pipe section is adapted to be connected to the second pipe section;
- wherein the first pipe section comprises:
  - at least one inner pipe;
  - at least one outer pipe; and
  - a space between the inner pipe and the outer pipe,
- wherein the second pipe section is a connection pipe, and
- wherein the space between the inner pipe and the outer pipe is adapted for receiving at least a portion of the connection pipe;
- the connection means further comprising:
- a closure means for short-circuiting or connecting an inner lumen of the at least one inner pipe with the space between the at least one inner pipe and the at least one outer pipe in fluid communication; and
- a means for moving the closure means, said means for moving the closure means being configured as a removable rinsing cap for exposing an opening of the inner pipe in order to establish the fluid connection.

29. The connection means according to claim 28, wherein the rinsing cap is adapted to be moved automatically for exposing with the aid of the means for moving the closure means.

30. A connection means for the fluid connection of at least one first fluid-conducting medical-technical system to one second fluid-conducting medical-technical system, comprising:
- at least one first pipe section of the first system;
- at least one second pipe section of the second system; and
- a pivotal mount for aligning the first pipe section and/or the second pipe section relative to each other,
- wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section;
- wherein the first pipe section comprises:
  - at least one inner pipe;
  - at least one outer pipe; and
  - a space between the inner pipe and the outer pipe,
- wherein the second pipe section is a connection pipe, and
- wherein the space between the inner pipe and the outer pipe is adapted for receiving at least a portion of the connection pipe;
- wherein inner pipe and the outer pipe are configured for axial displacement relative to each other.

31. The connection means according to claim 30, further comprising a means for axial displacement of the inner pipe and/or of the outer pipe relative to each other.

32. The connection means according to claim 31, wherein the means for axial displacement comprises a means for automatic axial displacement.

33. A connection means for the fluid connection of at least one first fluid-conducting medical-technical system to one second fluid-conducting medical-technical system, comprising:
- at least one first pipe section of the first system;
- at least one second pipe section of the second system;
- a pivotal mount for aligning the first pipe section and/or the second pipe section relative to each other; and
- hydrophilic surfaces arranged to contact fluid flow of the fluid connection to be obtained,
- wherein the first pipe section is adapted to be connected to the second pipe section via a widening for connecting the first pipe section to the second pipe section, wherein the widening has at least one of a spherical, globular, curved, arc-shaped and convex outer surface, and wherein the widening of the first pipe section is adapted to be received within the second pipe section.

\* \* \* \* \*